(12) United States Patent
Saliba et al.

(10) Patent No.: US 10,535,828 B2
(45) Date of Patent: Jan. 14, 2020

(54) MIXED CATION PEROVSKITE

(71) Applicant: OXFORD UNIVERSITY INNOVATION LIMITED, Oxford (GB)

(72) Inventors: Michael Saliba, Oxford (GB); David McMeekin, Oxford (GB); Henry James Snaith, Oxford (GB); Bernard Wenger, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 0 days.

(21) Appl. No.: 15/779,174

(22) PCT Filed: Nov. 25, 2016

(86) PCT No.: PCT/GB2016/053711
§ 371 (c)(1),
(2) Date: May 25, 2018

(87) PCT Pub. No.: WO2017/089819
PCT Pub. Date: Jun. 1, 2017

(65) Prior Publication Data
US 2018/0351123 A1   Dec. 6, 2018

Related U.S. Application Data

(60) Provisional application No. 62/424,040, filed on Nov. 18, 2016.

(30) Foreign Application Priority Data

Nov. 27, 2015   (GB) .................................. 1520972.9

(51) Int. Cl.
*H01L 29/08*   (2006.01)
*H01L 51/44*   (2006.01)
(Continued)

(52) U.S. Cl.
CPC .............. *H01L 51/447* (2013.01); *C07F 7/24* (2013.01); *H01L 51/0008* (2013.01);
(Continued)

(58) Field of Classification Search
None
See application file for complete search history.

(56) References Cited

U.S. PATENT DOCUMENTS

2015/0249170 A1*   9/2015   Snaith ................... H01L 51/422
                                                        136/256

FOREIGN PATENT DOCUMENTS

WO   2014045021 A1   3/2014
WO   2015092397 A1   6/2015
(Continued)

OTHER PUBLICATIONS

Amat, et al., Cation-Induced Band-Gap Tuning in Organohalide Perovskites: Interplay of Spin-Orbit Coupling and Octahedra Tilting, Nano Letters, 2014, 14:3608-3616.
(Continued)

*Primary Examiner* — Hung K Vu
(74) *Attorney, Agent, or Firm* — Quarles & Brady LLP

(57) ABSTRACT

The present invention relates to a crystalline compound comprising: (i) $Cs^+$ (caesium); (ii) $(H_2N-C(H)-NH_2)^+$ (formamidinium); (iii) one or more metal or metalloid dications [B]; and (iv) two or more different halide anions [X]. The invention also relates to a semiconductor device comprising a semiconducting material, which semiconducting material comprises the crystalline compound. The invention also relates to a process for producing a layer of the crystalline compound.

22 Claims, 24 Drawing Sheets

(51) Int. Cl.
*C07F 7/24* (2006.01)
*H01L 51/00* (2006.01)
*H01L 51/42* (2006.01)

(52) U.S. Cl.
CPC ...... *H01L 51/0032* (2013.01); *H01L 51/4226* (2013.01); *Y02E 10/549* (2013.01)

(56) References Cited

FOREIGN PATENT DOCUMENTS

| WO | 2015109647 A1 | 7/2015 |
|---|---|---|
| WO | 2016005758 A1 | 1/2016 |
| WO | 2016020699 A1 | 2/2016 |
| WO | 2016198889 A1 | 12/2016 |
| WO | 2017017441 A1 | 2/2017 |

OTHER PUBLICATIONS

Bailie, et al., Semi-Transparent Perovskite Solar Cells for Tandems with Silicon and CIGS, Energy & Environmental Science, 2015, 8(3):956-963.
Binek, et al., Stabilization of the Trigonal High-Temperature Phase of Formamidinium Lead Lodide, Journal of Physical Chemistry Letters, 2015, 6:1249-1253.
Burschka, et al., Sequential Deposition as a Route to High-Performance Perovskite-Sensitized Solar Cells, Nature, 2013, 499:316-319.
Catelli, et al., Bandgap Calculations and Trends of Organometal Halide Perovskites, APL Materials, 2014, 2:081514, 7 pages.
Choi, et al., Cesium-Doped Methylammonium Lead Iodide Perovskite Light Absorber for Hybrid Solar Cells, Nano Energy, 2014, 7:80-85.
De Wolf, et al., Organometallic Halide Perovskites: Sharp Optical Absorption Edge and Its Relation to Photovoltaic Performance, Journal of Physical Chemistry Letters, 2014, 5:1035-1039.
Eperon, et al., Formamidinium Lead Trihalide: A Broadly Tunable Perovskite for Efficient Planar Heterojunction Solar Cells, Energy & Environmental Science, 2014, 7:982-988.
Etgar, et al., Mesoscopic CH3NH3PbI3/TiO2 Heterojunction Solar Cells, Journal of the American Chemical Society, 2012, 134(42):17396-17399.
Green, et al., The Emergence of Perovskite Solar Cells, Nature Photonics, 2014, 8:506-514.
Haber, Manual on Catalyst Characterization, Pure & Appl. Chem., 1991, 63(9):1227-1246.
Hoke, et al., Reversible Photo-Induced Trap Formation in Mixed-Halide Hybrid Perovskites for Photovoltaics, Chemical Science, 2015, 6:613-617.
Jeon, et al., Solvent Engineering for High-Performance Inorganic-Organic Hybrid Perovskite Solar Cells, Nature Materials, 2014, 13:897-903.
Jeon, et al., Compositional Engineering of Perovskite Materials for High-Performance Solar Cells, Nature, 2015, 517:476-479.
Kagan, et al., Organic-Inorganic Hybrid Materials as Semiconducting Channels in Thin-Film Field-Effect Transistors, Science, 1999, 286:945-947.
Kojima, et al., Organometal Halide Perovskites as Visible-Light Sensitizers for Photovoltaic Cells, J. Am. Chem. Soc., 2009, 131:6050-6051.
Ku, et al., Full Printable Processed Mesoscopic CH3NH3PbI3/TiO2 Heterojunction Solar Cells with Carbon Counter Electrode, Scientific Reports, 2013, 3:3132, 5 pages.
Lee, et al., Efficient Hybrid Solar Cells Based on Meso-Superstructured Organometal Halide Perovskites, Science, 2012, 1228604, 5 pages.
Lee, et al., Formamidinium and Cesium Hybridization for Photo- and Moisture-Stable Perovskite Solar Cell, Advanced Energy Materials, 2015, 5:1501310, 9 pages.
Liu, et al., Efficient Planar Heterojunction Perovskite Solar Cells by Vapour Deposition, Nature, 2013, 501:395-398.
Loper, et al., Organic-Inorganic Halide Perovskite/Crystalline Silicon Four-Terminal Tandem Solar Cells, Phys. Chem. Chem. Phys., 2015, 17:1619-1629.
Mailoa, et al., A 2-Terminal Perovskite/Silicon Multijunction Solar Cell Enabled by a Silicon Tunnel Junction, Applied Physics Letters, 2015, 106:121105, 4 pages.
Mazzarella, et al., p-type Microcrystalline Silicon Oxide Emitter for Silicon Heterojunction Solar Cells Allowing Current Densities Above 40 mA/cm2, Applied Physics Letters, 2015, 106:023902, 5 pages.
Noh, et al., Chemical Management for Colorful, Efficient, and Stable Inorganic-Organic Hybrid Nanostructured Solar Cells, Nano Letters, 2013, 13(4):1764-1769.
Pellet, et al., Mixed-Organic-Cation Perovskite Photovoltaics for Enhanced Solar-Light Harvesting, Angew. Chem. Int. Ed., 2014, 53:3151-3157.
Polman, et al., Photonic Design Principles for Ultrahigh-Efficiency Photovoltaics, Nature Materials, 2012, 11:174-177.
Rau, Reciprocity Relation Between Photovoltaic Quantum Efficiency and Electroluminescent Emission of Solar Cells, Physical Review B, 2007, 76:085303, 8 pages.
Rouquerol, et al., Recommendations for the Characterization of Porous Solids, Pure & Appl. Chem., 1994, 66(8):1739-1758.
Sadhanala, et al., Preparation of Single-Phase Films of CH3NH3Pb(I1_xBrx)3 with Sharp Optical Band Edges, Journal of Physical Chemistry Letters, 2014, 5:2501-2505.
Saliba, et al., Cesium-Containing Triple Cation Perovskite Solar Cells: Improved Stability, Reproducibility and High Efficiency, Energy & Environmental Science, 2016, 9:1989-1997.
Shah, et al., Photovoltaic Technology: The Case for Thin-Film Solar Cells, Science, 1999, 285:692-698.
Shockley, et al., Detailed Balance Limit of Efficiency of p-n Junction Solar Cells, Journal of Applied Physics, 1961, 32(3):510-519.
Sing, et al., Reporting Physisorption Data for Gas/Solid Systems with Special Reference to the Determination of Surface Area and Porosity, Pure & Appl. Chem., 1985, 57(4):603-619.
Sivaram, et al., Out-Shining Silicon, Scientific American, 2015, 313(1):54-59.
Snaith, Estimating the Maximum Attainable Efficiency in Dye-Sensitized Solar Cells, Advanced Functional Materials, 2010, 20:13-19.
Stoumpos, et al., Semiconducting Tin and Lead Iodide Perovskites with Organic Cations: Phase Transitions, High Mobilities, and Near-Infrared Photoluminescent Properties, Inorganic Chemistry, 2013, 52:9019-9038.
Stranks, et al., Metal-Halide Perovskites for Photovoltaic and Light-Emitting Devices, Nature Nanotechnology, 2015, 10:391-402.
Tvingstedt, et al., Radiative Efficiency of Lead Iodide Based Perovskite Solar Cells, Scientific Reports, 2014, 4:607, 7 pages.
Xu, et al., Highly Ordered Mesoporous Carbon for Mesoscopic CH3NH3PbI3/TiO2 Heterojunction Solar Cell, Journal of Materials Chemistry A, 2014, 2:8607-8611.
Yang, et al., High-Performance Photovoltaic Perovskite Layers Fabricated Through Intramolecular Exchange, Science, 2015, 348(6240):1234-1237.
Yi, et al. Entropic Stabilization of Mixed A-Cation ABX3 Metal Halide Perovskites for High Performance Perovskite Solar Cells, Energy & Environmental Science, 2016, 9:656-662.
Yin, et al., Halide Perovskite Materials for Solar Cells: A Theoretical Review, Journal of Materials Chemistry A, 2015, 3:8926-8942.

\* cited by examiner

MIXED CATION PEROVSKITE

CROSS-REFERENCE TO RELATED APPLICATIONS

This application represents the national stage entry of PCT International Application No. PCT/GB2016/053711 filed Nov. 25, 2016, which claims priority to Great Britain Patent Application 1520972.9 filed Nov. 27, 2015, which claims priority to U.S. Provisional Patent Application 62/424,040 filed Nov. 18, 2016, the contents of which are hereby incorporated herein by reference for all purposes.

FIELD OF THE INVENTION

The present invention relates to a crystalline compound useful as a semiconductor material or a photoactive material. The invention also relates to a semiconductor device comprising a semiconducting material, which semiconducting material comprises the crystalline compound. A process for producing a layer of the crystalline compound is also described.

The work leading to this invention has received funding from the EPSRC through the Supergen Solar Energy Hub SuperSolar (EP/M024881/1) and (EP/M014797/1) the ERC through the Stg-2011 HYPER and the US Office of Naval Research (ONR).

BACKGROUND OF THE INVENTION

Terrestrial photovoltaic solar energy, predominantly based on single junction crystalline silicon, has a world record efficiency of 25% which represents an upper limit on the efficiency which we expect commercial modules eventually reach. To go beyond this performance, which is important in order to continuingly drive down the overall cost of generating electricity from sun light, more advanced concepts are required (Shockley et al., *J. Appl. Phys.* 32, 510 (1961); Yin et al., *J. Mater. Chem. A.* 3, 8926-8942 (2014) and Polman et al., *Nat. Mater.* 11, 174-7 (2012)). One such concept is to create a "tandem junction" by employing a wide band gap "top cell" in combination with a silicon "bottom cell", which could increase the realistically achievable efficiency to beyond 30% (Sivaram et al., *Sci. Am.* 313, 54-59 (2015)). For maximizing performance, a crystalline silicon (c-Si) bottom-cell with a band gap of 1.1 eV requires a top-cell material with a band gap of ~1.75 eV, in order to perfectly current-match both junctions (Shah et al., *Science.* 285, 692-699 (1999)).

However, to date, there has yet to be a suitable wide band gap top cell material for silicon or thin film technologies, which offers stability, high performance, and low cost. In recent years, metal halide perovskite-based solar cells have gained significant attention due to their high power conversion efficiencies (PCE) and low processing cost (C. R. Kagan, *Science.* 286, 945-947 (1999); Lee et al., *Science.* 338, 643-7 (2012); Liu et al., *Nature.* 501, 395-8 (2013); Burschka et al., *Nature.* 499, 316-9 (2013); Green et al., *Nat. Photonics.* 8, 506-514 (2014); Jeon et al., *Nat. Mater.* 13, 1-7 (2014); and Jeon et al., *Nature.* 517, 476-480 (2015)). An attractive feature of this material is the ability to tune its band gap from 1.48 to 2.3 eV (Noh et al., *Nano Lett.* 13, 1764-9 (2013) and Eperon et al., *Energy Environ. Sci.* 7, 982 (2014)) implying that one could potentially fabricate an ideal material for tandem cell applications.

Perovskite-based solar cells are generally fabricated using organic-inorganic trihalide perovskites with the formulation $ABX_3$, where A is the methylammonium ($CH_3NH_3$) (MA) or formamidinium ($HC(NH_2)_2$) (FA) cation, B is commonly lead (Pb), while X is a halide (Cl, Br, I). Although these perovskite structures offer high power conversion efficiencies (PCE), reaching over 20% PCE with band gaps of around 1.5 eV, fundamental issues have been discovered when attempting to tune their band gaps to hit the optimum 1.7 to 1.8 eV range (Yang et al., *Science.* 348, 1234-1237 (2015)). In the case of methylammonium lead trihalide ($MAPb(I_{(1-y)}Br_3)_3$), Hoke et al. (*Chem. Sci.* 6, 613-617 (2014)) reported that light-soaking induces a halide segregation within the absorbing material. The formation of iodide-rich domains with lower band gap results in an increase in sub-gap absorption and a red-shift of photoluminescence (PL). The lower band gap regions limit the voltage attainable with such a material, so this band gap "photo-instability" limits the use of $MAPb(I_{(1-y)}Br_3)_3$ in tandem devices. In addition, when considering real-world applications, it has been shown that $MAPbI_3$ is inherently thermally unstable at 85° C. even in an inert atmosphere—this is the temperature that international regulations require a commercial PV product to be capable of withstanding.

Concerning the more thermally stable $FAPbX_3$ perovskite, open-circuit voltage ($V_{OC}$) pinning has also been observed in $FAPb(I_{(1-x)}Br_x)_3$ devices, where an increase in optical band gap did not result in an expected increase in $V_{OC}$. Furthermore, as the iodide is substituted with bromide, a crystal phase transition is observed from a trigonal to a cubic structure: in compositions close to the transition, the material appears unable to crystallize, resulting in an apparently "amorphous" phase with high levels of energetic disorder and unexpectedly low absorption. These compositions additionally have much lower charge-carrier mobilities in the range of 1 $cm^2/Vs$, in comparison to over 20 $cm^2/Vs$ in the neat iodide perovskite, and higher recombination rates than in the crystalline material. This is not an issue for high efficiency single junction solar cells since they can be fabricated with the iodine rich, phase stable material, but disadvantageously for tandem applications, this occurs right at the Br composition needed to form the desired top-cell band gap of ~1.7 to 1.8 eV.

Nevertheless, perovskite/silicon tandem solar cells have already been reported in a 4-terminal and 2-terminal architectures (Bailie et al., *Energy Environ. Sci.* 8, 956-963 (2015); Löper et al., *Phys. Chem. Chem. Phys.* 17, 1619-29 (2015); and Mailoa et al., *Appl. Phys. Lett.* 106, 121105 (2015)). However, their reported efficiencies have yet to surpass the optimized single-junction efficiencies, in part due to non-ideal absorber band gaps having been employed. To avoid the halide segregation problem, it is possible to form a lower band gap triiodide perovskite material and current-match the top and bottom junctions in a monolithic architecture by simply reducing the thickness of the top-cell. However, this method results in a non-ideal efficiency.

Choi et al. (*Nano Energy* (2014) 7, 80-85) describes mixed cation perovskite compounds comprising both cesium and methylammonium. Lee et al. (*Adv. Energy Mater.* (2015) 5, 1501310) describes mixed cation perovskite compounds comprising both cesium and formamidinium. Pellet et al. (*Angew. Chem. Int. Ed.* (2014) 53, 3151-3157) describes mixed cation perovskite compounds comprising both methylammonium and formamidinium. Jeon et al. (*Nature* (2015) 517, 476-479) describes mixed cation/mixed halide perovskite compounds comprising both methylammonium and formamidinium and both iodide and bromide. However, these perovskite do not yet provide the full tunability and stability required for use in tandem cells.

There is a need to develop a new photoactive material which has a tunable band gap and does not have the issues of halide segregation or thermal instability.

SUMMARY OF THE INVENTION

The inventors have discovered a perovskite composition which delivers the ideal absorber material for stable and efficient hybrid tandem solar cells. In particular, the inventors have addressed the issues of forming a photo-stable FA based perovskite with the ideal band gap for tandem applications by partially substituting the formamidinium cation with caesium. The remarkable observation has been made that the phase instability region is then entirely eliminated in the iodide to bromide compositional range.

The invention therefore provides a crystalline compound comprising:
(i) Cs';
(ii) $(H_2N-C(H)=N H_2)'$;
(iii) one or more metal or metalloid dications [B]; and
(iv) two or more different halide anions [X].

The invention also provides a semiconducting material comprising the crystalline compound of the invention.

The invention also provides a semiconductor device comprising a semiconducting material, which semiconducting material comprises a crystalline compound, which crystalline compound comprises:
(i) Cs';
(ii) $(H_2N-C(H)=NH_2)$;
(iii) one or more metal or metalloid dications [B]; and
(iv) two or more different halide anions [X].

Further provided by the invention is a process for producing a layer of a crystalline compound, which crystalline compound comprises:
(i) Cs';
(ii) $(H_2N-C(H)=NH_2-)$;
(iii) one or more metal or metalloid dications [B]; and
(iv) a first halide anion X; and
(v) a second halide anion X',
which process comprises:
(a) disposing on a substrate a precursor composition comprising:
CsX and/or CsX';
$(H_2N-C(H)=NH_2)X$ and/or $(H_2N-C(H)=NH_2)X'$;
$BX_2$ and/or $BX'_2$.

DETAILED DESCRIPTION OF THE INVENTION

Figure 1:
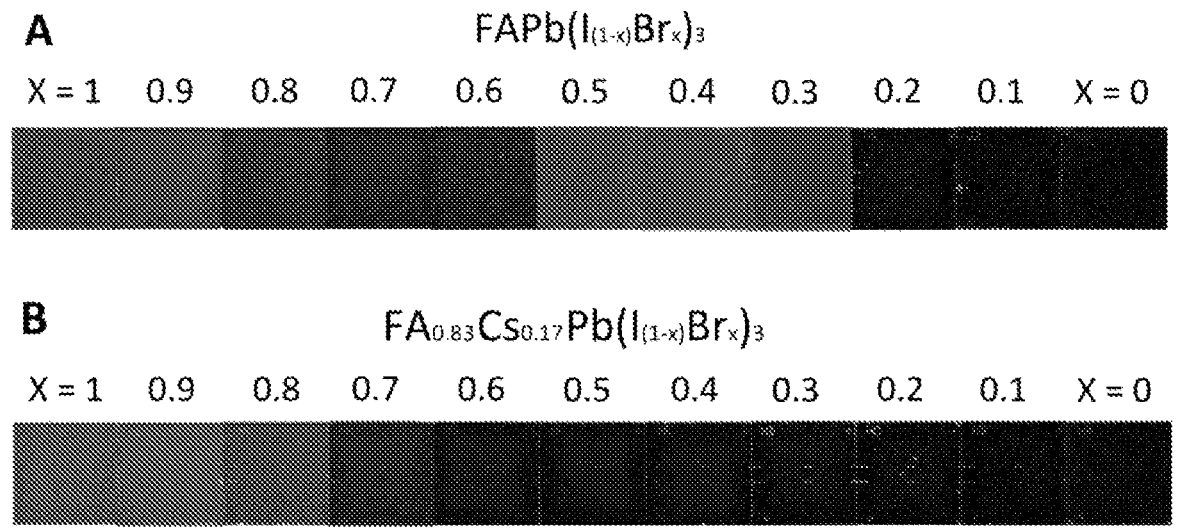
FIG. 1 shows (A) a photograph of perovskite films with Br composition increasing from X=0 to 1 for the $FAPb(I_{(1-x)}Br_x)_3$ system and (B) for the $FA_{0.83}Cs_{0.17}Pb(I_{(1-x)}Br_x)_3$ system.

The invention provides a crystalline compound comprising: (i) Cs'; (ii) (H$_2$N—C(H)=NH$_2$)'; (iii) one or more metal or metalloid dications [B]; and (iv) two or more different halide anions [X]. Thus, the crystalline compound is a crystalline compound having a formula which comprises Cs', (H$_2$N—C(H)=NH$_2$)', [B] and [X]. For instance, the crystalline compound may be a compound of formula Cs$_p$(H$_2$N—C(H)=NH$_2$)$_q$[B]$_r$[X]$_s$ where p, q, r and s are numbers from 0.01 to 8.0. The crystalline compound may in some cases comprise additional ions.

A crystalline compound is a compound defined by a formula comprising two or more ions, wherein the ions in the compound are arranged in an extended crystal structure. For instance, sodium chloride (NaCl) is a crystalline compound, the formula of which comprises Na$^+$ and Cl$^-$, and where these two ions are arranged in an extended crystal structure (the rock salt structure). Bonding between atoms and/or ions within a crystalline compound is typically intermediate between fully ionic and fully covalent bonding, although there is a predominance of ionic bonding.

An amount of a crystalline compound typically comprises crystallites of the crystalline compound, i.e. a plurality of single crystal domains of the crystalline compound, which may be in the form of a powder or a solid. In a solid comprising a plurality of crystallites of a crystalline compound (which may be referred to as a polycrystalline solid), grain boundaries will be present between adjacent crystallites where there is a discontinuity in the extended crystal structure. A crystalline compound may be in the form of a single crystal.

The halide anions [X] may be selected from I$^-$, Br$^-$, Cl$^-$ and F$^-$. Typically, the two or more different halide anions [X] are selected from I$^-$, Br$^-$ and Cl$^-$. Preferably, the two or more different halide anions [X] are I$^-$ and Br$^-$. In that case, the crystalline compound comprises both I$^-$ and Br$^-$. Alternatively, the two or more different halide anions [X] may be Br$^-$ and Cl$^-$. The two or more different halide anions may be present in any proportion. For instance, [X]$_3$ may correspond to (I, Br)$_3$ where I and Br are in any proportion, or a proportion as further defined below. The two or different halide anions will all occupy X sites within the structure of the crystalline compound. The halide anions may be ordered or disordered within those X sites.

The metal or metalloid dications may be dications derived from any metal in groups 1 to 16 of the periodic table of the elements or any of the metalloids. Metalloids are usually taken to be following elements: B, Si, Ge, As, Sb, Te and Po. Typically, the one or more metal or metalloid dications are selected from Ca$^{2+}$, Sr$^{2+}$, Cd$^{2+}$, cu$^{2+}$, Ni$^{2+}$, Mn$^{2+}$, Fe$^{2+}$, Co$^{2+}$, Pd$^{2+}$, Ge$^{2+}$, Sn$^{2+}$, Pb$^{2+}$, Yb$^{2+}$ and Eu$^{2+}$. Preferably, the one or more metal or metalloid dications [B] are selected from Pb$^{2+}$, Sn$^{2+}$, Ge$^{2+}$ and Cu$^{2+}$. More preferably, the one or more metal or metalloid dications [B] are Pb$^{2+}$, i.e. the formula of the crystalline compound comprises only Pb$^{2+}$ as the metal or metalloid dication.

Typically, the crystalline compound is a perovskite compound having a three dimensional perovskite structure and comprising (i) Cs'; (ii) (H₂N—C(H)=NH₂)⁺; (iii) one or more metal or metalloid dications [B]; and (iv) two or more different halide anions [X]. Thus, the crystalline compound typically has the three-dimensional crystal structure which is related to that of CaTiO₃. The structure of CaTiO₃ can be represented by the formula ABX₃, wherein A and B are cations of different sizes and X is an anion. In the unit cell for a perfect ABX₃ structure, the A cations are at (0,0,0), the B cations are at (1/2, 1/2, 1/2) and the X anions are at (1/2, 1/2, 0). The A cation is usually larger than the B cation. The skilled person will appreciate that when A, B and X are varied, the different ion sizes may cause the structure of the perovskite material to distort away from the structure adopted by CaTiO₃ to a lower-symmetry distorted structure. Such distorted structures still comprise a three dimensional array of BX₆ octahedra and are still examples of the three dimensional perovskite structure. The skilled person will appreciate that the perovskite compound can be represented by the formula [A][B][X]₃, wherein [A] is at least one cation, [B] is at least one cation and [X] is at least one anion. When the perovskite comprises more than one A cation (e.g. wherein [A] is (A¹, A²) or (A¹, A², A³)), the different A cations may distributed over the A sites in an ordered or disordered way. When the perovskite comprises more than one B cation, the different B cations may distributed over the B sites in an ordered or disordered way. When the perovskite comprise more than one X anion, the different X anions may distributed over the X sites in an ordered or disordered way. The symmetry of a perovskite comprising more than one A cation, more than one B cation or more than one X cation, will be lower than that of CaTiO₃.

The crystalline compound is often a perovskite compound of formula (I):

$$Cs_x(H_2N-C(H)=NH_2)_{(1-x)}[B][X]_3 \quad (I);$$

wherein: [B] is the one or more metal or metalloid dications; [X] is the two or more different halide anions; and x is from 0.01 to 0.99.

Preferably, the crystalline compound is a perovskite compound of formula (II):

$$Cs_x(H_2N-C(H)=NH_2)_{(1-x)}[B]X_{3y}X'_{3(1-y)} \quad (II);$$

wherein: [B] is the one or more metal or metalloid dications; X is a first halide anion selected from I⁻, Br⁻, Cl⁻ and F⁻; X' is a second halide anion which is different from the first halide anion and is selected from I⁻, Br⁻, Cl⁻ and F⁻; x is from 0.01 to 0.99; and y is from 0.01 to 0.99. Typically X is a first halide anion selected from I⁻, Br⁻ and Cl⁻ and X' is a second halide anion which is different from the first halide anion and is selected from I⁻, Br⁻ and Cl⁻. Preferably, in formula (II), [B] is Pb²⁺ and the crystalline compound is of formula $Cs_x(H_2N-C(H)=NH_2)_{(1-x)}PbX_{3y}X'_{3(1-y)}$.

Preferably, X is Br and X' is I⁻. Alternatively, X is Cl⁻ and X' is I⁻, or X is Cl⁻ and X' is Br⁻.

Typically, in formula (I), (II) or (III), x is from 0.05 to 0.50. Preferably, x is from 0.10 to 0.30. More preferably, x is from 0.15 to 0.20.

Typically, in formula (II) or (III), y is from 0.01 to 0.70. Preferably, y is from 0.20 to 0.60. More preferably is from 0.30 to 0.50.

For instance, in formula (II) or (III), x may be from 0.10 to 0.30 and y may be from 0.20 to 0.60.

Preferably, the crystalline compound is a perovskite compound of formula (III):

$$Cs_x(H_2N-C(H)=NH_2)_{(1-x)}PbBr_{3y}I_{3(1-y)} \quad (III);$$

wherein: x is from 0.15 to 0.20; and y is from 0.30 to 0.50.

Often, the crystalline compound is of formula $Cs_{0.2}(H_2N-C(H)=NH_2)_{0.8}Pb(Br_{0.4}I_{0.6})_3$, where the proportion of each ion is to 1 decimal place. As such, the proportion of Cs⁻ may be from 0.150 to 0.249, the proportion of (H₂N—C(H)=NH₂)⁻ may be from 0.750 to 0.849, the proportion of Br may be from 0.350 to 0.449 and the proportion of I⁻ may be from 0.50 to 0.649. The proportion of I⁻ may be from 0.550 to 0.649.

The crystalline compound may be a compound of formula $Cs_{0.2}(H_2N-C(H)=NH_2)_{0.8}Pb(Br_{0.4}I_{0.6})_3$. In one embodiment, the crystalline compound is $Cs_{0.17}(H_2N-C(H)=NH_2)_{0.83}Pb(Br_{0.4}I_{0.6})_3$. For instance, the crystalline compound may be $Cs_{0.175}(H_2N-C(H)=NH_2)_{0.825}Pb(Br_{0.4}I_{0.6})_3$.

As the skilled person will appreciate, there may be some minor variations in the stoichiometry of the crystalline compound, for instance within different regions of a solid form of the crystalline compound. However, such solid forms having some variation in the stoichiometry of the crystalline compound will still contain an amount of the specific crystalline compounds described herein. Typically, a crystalline compound according to the invention may have an average stoichiometry corresponding to the stoichiometry as set out in a formulae described herein. For instance, a solid form of a crystalline compound according to the invention may comprise from 15 mol % to 20 mol % of Cs relative to the amount of Pb and from 85 mol % to 80 mol % of H₂N—C(H)=NH₂ relative to the amount of Pb.

Figure 22:
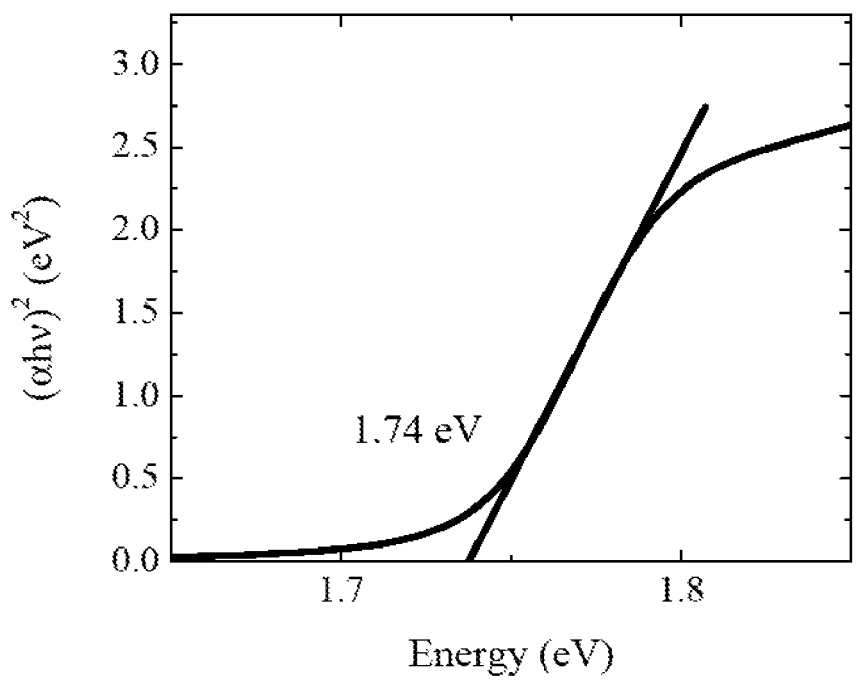
FIG. 22 shows Tauc plot of $FA_{0.83}Cs_{0.17}Pb(I_{0.6}Br_{0.4})_3$ assuming direct band gap and showing determination of estimated band gap from intercept.

The crystalline compound according to the invention has a fully tunable band gap and as such is well suited to use as a photoactive material in tandem with a second photoactive material such as silicon. The crystalline compound typically has a band gap of from 1.25 to 2.25 eV. Preferably, the crystalline compound has a band gap of from 1.5 to 2.0 eV. The crystalline compound may, for instance, have a band gap of from 1.7 to 1.8 eV. The band gap can be determined by making a Tauc plot, as described in Tauc, J., Grigorovici, R. & Vancu, a. Optical Properties and Electronic Structure of Amorphous Germanium. Phys. Status Solidi 15, 627-637 (1966) where the square of the product of absorption coefficient times photon energy is plotted on the y-axis against photon energy on the x-axis with the straight line intercept of the absorption edge with the x-axis giving the optical band gap of the semiconductor (for instance as shown in FIG. 22). The band gap is typically as measured at 20° C.

The crystalline compound may be in the form of a solid layer of the crystalline compound, for instance a layer without open porosity. The crystalline compound may be in the form of a compact layer of the crystalline compound.

The term "porous", as used herein, refers to a material within which pores are arranged. Thus, for instance, in a porous scaffold material the pores are volumes within the scaffold where there is no scaffold material. The individual pores may be the same size or different sizes. The size of the pores is defined as the "pore size". The limiting size of a pore, for most phenomena in which porous solids are involved, is that of its smallest dimension which, in the absence of any further precision, is referred to as the width of the pore (i.e. the width of a slit-shaped pore, the diameter of a cylindrical or spherical pore, etc.). To avoid a misleading change in scale when comparing cylindrical and slit-shaped pores, one should use the diameter of a cylindrical pore (rather than its length) as its "pore-width" (J. Rouquerol et al., "Recommendations for the Characterization of Porous Solids", Pure & Appl. Chem., Vol. 66. No. 8, pp. 1739-1758, 1994). The following distinctions and definitions were adopted in previous IUPAC documents (K. S. W. Sing, et al, Pure and Appl. Chem., vol. 57, n04, pp 603-919, 1985; and IUPAC "Manual on Catalyst Characterization", J. Haber. Pure and Appl. Chem., vol. 63, pp. 1227-1246, 1991); micropores have widths (i.e. pore sizes) smaller than 2 nm; Mesopores have widths (i.e. pore sizes) of from 2 nm to 50 nm; and Macropores have widths (i.e. pore sizes) of greater than 50 nm. In addition, nanopores may be considered to have widths (i.e. pore sizes) of less than 1 nm.

Pores in a material may include "closed" pores as well as open pores. A closed pore is a pore in a material which is a non-connected cavity, i.e. a pore which is isolated within the material and not connected to any other pore and which cannot therefore be accessed by a fluid (e.g. a liquid, such as a solution) to which the material is exposed. An "open pore" on the other hand, would be accessible by such a fluid. The concepts of open and closed porosity are discussed in detail in J. Rouquerol et al., "Recommendations for the Characterization of Porous Solids", Pure & Appl. Chem., Vol. 66, No. 8, pp. 1739-1758, 1994.

Open porosity, therefore, refers to the fraction of the total volume of the porous material in which fluid flow could effectively take place. It therefore excludes closed pores. The term "open porosity" is interchangeable with the terms "connected porosity" and "effective porosity", and in the art is commonly reduced simply to "porosity".

The term "without open porosity", as used herein, therefore refers to a material with no effective open porosity. Thus, a material without open porosity typically has no macropores and no mesopores. A material without open porosity may comprise micropores and nanopores, however. Such micropores and nanopores are typically too small to have a negative effect on a material for which low porosity is desired.

The term "compact layer", as used herein, refers to a layer without mesoporosity or macroporosity. A compact layer may sometimes have microporosity or nanoporosity.

The invention also provides particles comprising the crystalline compound. Thus, the crystalline compound may be in the form of particles comprising the crystalline compound. Typically, such particles have a number average particle size of less than or equal to 1.0 mm. The particle size of a particle is the diameter of a sphere having the same volume as the particle. This may be measured by laser diffraction.

The particles may be microparticles, mesoparticles or nanoparticles. Microparticles are particles having a number average particle size of from $1.0 \times 10^{-7}$ to $1.0 \times 10^{-4}$ m (i.e. from 0.1 to 100 μm). Mesoparticles are particles having a number average particle size of from $1.0 \times 10^{-8}$ to $1.0 \times 10^{-6}$ m (i.e. from 10 to 1000 nm). Nanoparticles are particles having a number average particle size of from $1.0 \times 10^{-9}$ to $1.0 \times 10^{-7}$ m (i.e. from 1.0 to 100 nm).

The particles of the crystalline compound may be present in a colloid. Such a colloid may comprise a continuous liquid or solid phase and, disposed in the continuous phase, a plurality of the particles of the crystalline compound.

The invention also provides a semiconducting material comprising a crystalline compound as defined herein. The semiconducting material is preferably a photoactive material.

The term "semiconductor" or "semiconducting material", as used herein, refers to a material with electrical conductivity intermediate in magnitude between that of a conductor and a dielectric. A semiconductor may be an negative (n)-type semiconductor, a positive (p)-type semiconductor or an intrinsic (i) semiconductor. Examples of semiconducting materials include photoactive materials. The term "photoactive material", as used herein, refers to a material which either (i) absorbs light, which may then generate free charge carriers; or (ii) accepts charge, both electrons and holes, which may subsequently recombine and emit light. A photoabsorbent material is a material which absorbs light, which may then generate free charge carriers (e.g electrons and holes). A "photoemissive material" is a material which absorbs light of energies higher than band gap and remits light at energies at the band gap.

The semiconducting material typically comprises greater than or equal to 80% by weight of the crystalline compound. The semiconducting material may for instance comprise greater than or equal to 90% by weight of the crystalline compound.

The semiconducting material may be in the form of a layer, for instance a compact layer of the semiconducting material.

The invention also provides a semiconductor device comprising a semiconducting material, which semiconducting material comprises a crystalline compound, which crystalline compound comprises: (i) Cs'; (ii) $(H_2N—C(H)=NH_2)'$; (iii) one or more metal or metalloid dications [B]; and (iv) two or more different halide anions [X]. The crystalline compound may be as defined herein, for instance a compound of formula (III).

The term "semiconductor device", as used herein, refers to a device comprising a functional component which functional component comprises a semiconductor material. This term may be understood to be synonymous with the term "semiconducting device". Examples of semiconductor devices include an optoelectronic device, a photovoltaic device, a solar cell, a photo detector, a photodiode, a photosensor, a chromogenic device, a transistor, a light-sensitive transistor, a phototransistor, a solid state triode, a battery, a battery electrode, a capacitor, a super-capacitor, a light-emitting device and a light-emitting diode. The term "optoelectronic device", as used herein, refers to devices which source, control, detect or emit light. Light is understood to include any electromagnetic radiation. Examples of optoelectronic devices include photovoltaic devices, photodiodes (including solar cells), phototransistors, photomultipliers, photoresistors, light emitting devices, light emitting diodes, lasers and charge injection lasers.

The semiconductor device is typically an optoelectronic device. Preferably, the semiconductor device is a photovoltaic device, a photodetector or a light-emitting device. More preferably, the semiconductor device is a photovoltaic device (for instance a solar cell).

The semiconductor device typically comprises a layer of the semiconducting material. The layer of said semiconducting material may for instance have a thickness of from 5 nm to 10000 nm. Typically, the semiconductor device comprises a layer of the semiconducting material, which layer preferably has a thickness of from 5 nm to 1000 nm. Preferably, the layer of the semiconducting material has a thickness of from 100 nm to 700 nm, for instance from 200 nm to 500 nm. The layer of the semiconducting material may consist, or consist essentially of (e.g. greater than or equal to 99 wt %) a layer of the compound having a thickness of from 100 nm to 700 nm. In some devices, the layer may be a thin sensitising layer, for instance having a thickness of from 5 nm to 50 nm. In devices wherein the layer of said semiconducting material forms a planar heterojunction with an n-type or p-type region, the layer of said photoactive material may have a thickness of greater than or equal to 100 nm.

Preferably, the layer of said photoactive material has a thickness of from 100 nm to 700 nm, for instance from 200 nm to 500 nm.

Typically, the semiconductor device comprises: an n-type region comprising at least one n-type layer; a p-type region comprising at least one p-type layer; and, disposed between the n-type region and the p-type region; a layer of said semiconducting material. An n-type layer is typically a layer of an n-type semiconductor. A p-type layer is typically a layer of a p-type semiconductor.

The n-type region comprises at least one n-type layer. The n-type region may alternatively comprise an n-type layer and an n-type exciton blocking layer. Such an n-type exciton blocking layer is typically disposed between the n-type layer and the layer(s) comprising the semiconducting material. The n-type region may have a thickness of from 50 nm to 1000 nm. For instance, the n-type region may have a thickness of from 50 nm to 500 nm, or from 100 nm to 500 nm.

Preferably, the n-type region comprises a compact layer of an n-type semiconductor.

The n-type semiconductor may be selected from a metal oxide, a metal sulphide, a metal selenide, a metal telluride, a perovskite, amorphous Si, an n-type group IV semiconductor, an n-type group III-V semiconductor, an n-type group II-VI semiconductor, an n-type group I-VII semiconductor, an n-type group IV-VI semiconductor, an n-type group V-VI semiconductor, and an n-type group II-V semiconductor, any of which may be doped or undoped. Typically, the n-type semiconductor is selected from a metal oxide, a metal sulphide, a metal selenide, and a metal telluride. For instance, the n-type region may comprise an inorganic material selected from oxide of titanium, tin, zinc, niobium, tantalum, tungsten, indium, gallium, neodymium, palladium, or cadmium, or an oxide of a mixture of two or more of said metals. For instance, the n-type layer ma) comprise $TiO_2$, $SnO_2$, ZnO, $Nb_2O_5$, $Ta_2O_5$, $WO_3$, $W_2O_5$, $In_2O_3$, $Ga_2O_3$, $Nd_2O_3$, PbO, or CdO.

Typically, the n-type region comprises $SnO_2$ or $TiO_2$, for instance a compact layer of $TiO_2$ or $SnO_2$. Often, the n-type region also comprises a layer of a fullerene or a fullerene derivative (for instance $C_{60}$ or Phenyl-C61-butyric acid methyl ester (PCBM)).

The p-type region comprises at least one p-type layer. The p-type region may alternatively comprise an p-type layer and a p-type exciton blocking layer. Such a p-type exciton blocking layer is typically disposed between the p-type layer and the layer(s) comprising the semiconducting material. The p-type region may have a thickness of from 50 nm to 1000 nm. For instance, the p-type region may have a thickness of from 50 nm to 500 nm, or from 100 nm to 500 nm.

Preferably, the p-type region comprises a compact layer of a p-type semiconductor Suitable p-type semiconductors may be selected from polymeric or molecular hole transporters. The p-type layer employed in the semiconductor device of the invention may for instance comprise spiro-OMeTAD (2,2',7,7'-tetrakis-(N,N-di-p-methoxyphenylamine)9,9'-spirobifluorene)), P3HT (poly(3-hexylthiophene)), PCPDTBT (Poly[2,1,3-benzothiadiazole-4,7-diyl[4,4-bis(2-ethylhexyl)-4H-cyclopenta[2,1-b:3,4-b']dithiophene-2,6-diyl]), PVK (poly(N-vinylcarbazole)), HTM-TFSI (1-hexyl-3-methylimidazolium bis(trifluoromethylsulfonyl)imide), Li-TFSI (lithium bis(trifluoromethanesulfonyl)imide) or tBP (tert-butylpyridine). The p-type region may comprise carbon nanotubes. Usually, the p-type material is selected from spiro-OMeTAD, P3HT, PCPDTBT and PVK. Preferably, the p-type layer employed in the optoelectronic device of the invention comprises spiro-OMeTAD.

In some embodiments, the p-type layer may comprise an inorganic hole transporter. For instance, the p-type layer may comprise an inorganic hole transporter comprising an oxide of nickel, vanadium, copper or molybdenum; CuI, CuBr, CuSCN, $Cu_2O$, CuO or CIS; a perovskite; amorphous Si; a p-type group IV semiconductor, a p-type group III-V semiconductor, a p-type group III-VI semiconductor, a p-type group I-VII semiconductor, a p-type group IV-VI semiconductor, a p-type group V-VI semiconductor, and a p-type group II-V semiconductor, which inorganic material may be doped or undoped. The p-type layer may be a compact layer of said inorganic hole transporter.

The layer of the semiconducting material typically forms a planar heterojunction with the n-type region or the p-type region. The layer of the semiconducting material typically forms a first planar heterojunction with the n-type region and a second planar heterojunction with the p-type region. This forms a planar heterojunction device. The term "planar heterojunction" as used herein refers to a junction between two regions where one region does not infiltrate the other. This does not require that the junction is completely smooth, just that one region does not substantially infiltrate pores in the other region.

In some embodiments, it is desirable to have a porous scaffold material present. The layer of a porous scaffold is usually in contact with a compact layer of a semiconductor material, for instance an n-type compact layer or a p-type compact layer. The layer of a porous scaffold is usually also in contact with the semiconducting material. The scaffold material is typically mesoporous or macroporous. The scaffold material may aid charge transport from the semiconducting material to an adjacent region. The scaffold material may also, or alternatively, aid formation of the layer of the semiconducting material during device construction. The porous scaffold material is typically infiltrated by the semiconducting material.

Thus, in some embodiments, the semiconductor device comprises:
  an n-type region comprising at least one n-type layer;
  a p-type region comprising at least one p-type layer; and, disposed between the n-type region and the p-type region;
  (i) a porous scaffold material; and
  (ii) said semiconducting material in contact with the scaffold material.

Typically, the semiconducting material in the first layer is disposed in pores of the scaffold material. The scaffold material is typically mesoporous. The scaffold material may be macroporous.

Typically, the porous scaffold material comprises a dielectric material or a charge-transporting material. The scaffold material may be a dielectric scaffold material. The scaffold material may be a charge-transporting scaffold material. The porous scaffold material may be an electron-transporting material or a hole-transporting scaffold material. n-type semiconducting materials are examples of electron-transporting materials. p-type semiconductors are examples of hole-transporting scaffold materials. Preferably, the porous scaffold material is a dielectric scaffold material or an electron-transporting scaffold material (e.g. an n-type scaffold material). The porous scaffold material may be a charge-transporting scaffold material (e.g. an electron-transporting material such as titania, or alternatively a hole transporting material) or a dielectric material, such as alumina. The term "dielectric material", as used herein, refers to material which is an electrical insulator or a very poor conductor of electric current. The term dielectric therefore excludes semiconducting materials such as titania. The term dielectric, as used herein, typically refers to materials having a band gap of equal to or greater than 4.0 eV. (The band gap of titania is about 3.2 eV.)

The porous scaffold material typically comprises an n-type semiconductor or a dielectric material. For instance, the device may comprise a layer of said porous scaffold material, where the porous scaffold material comprises an n-type semiconductor.

The porous scaffold is typically in the form of a layer. For instance, the porous scaffold may be a layer of porous scaffold material, typically having a thickness of from 5 nm to 500 nm, for instance from 10 nm to 200 nm.

In some embodiments, the semiconductor device comprises:
- an n-type region comprising at least one n-type layer;
- a p-type region comprising at least one p-type layer; and, disposed between the n-type region and the p-type region;
  (i) a first layer which comprises a porous scaffold material and said semiconducting material; and
  (ii) a capping layer disposed on said first layer, which capping layer is a layer of said semiconducting material without open porosity,
  wherein the semiconducting material in the capping layer is in contact with the semiconducting material in the first layer.

In some embodiments, the scaffold material is porous and the semiconducting material in the first layer is disposed in pores of the scaffold material. The effective porosity of said scaffold material is usually at least 50%. For instance, the effective porosity may be about 70%. In one embodiment, the effective porosity is at least 60%, for instance at least 70%.

Typically, the semiconducting material (or photoactive material) in the first layer contacts one of the p-type and n-type regions, and the semiconducting material in the capping layer contacts the other of the p-type and n-type regions. The semiconducting material in the capping layer typically forms a planar heterojunction with the p-type region or the n-type region.

In one embodiment, the semiconducting material in the capping layer contacts the p-type region, and the semiconducting material in the first layer contacts the n-type region. In another embodiment, the semiconducting material in the capping layer contacts the n-type region, and the semiconducting material in the first layer contacts the p-type region (for instance in an inverted device).

The thickness of the capping layer is usually greater than the thickness of the first layer. The majority of any photoactivity (e.g. light absorption or light emission) therefore usually occurs in a capping layer.

The thickness of the capping layer is typically from 10 nm to 100 µm. More typically, the thickness of the capping layer is from 10 nm to 10 µm. Preferably, the thickness of the capping layer is from 50 nm to 1000 nm, or for instance from 100 nm to 700 nm. The thickness of the capping layer may be greater than or equal to 100 nm.

The thickness of the first layer, on the other hand, is often from 5 nm to 1000 nm. More typically, it is from 5 nm to 500 nm, or for instance from 30 nm to 200 nm.

The semiconductor device typically further comprises one or more first electrodes and one or more second electrodes. The one or more first electrodes are typically in contact with the n-type region, if such a region is present. The one or more second electrodes are typically in contact with the p-type region, if such a region is present. Typically; the one or more first electrodes are in contact with the n-type region and the one or more second electrodes are in contact with the p-type region; or the one or more first electrodes are in contact with the p-type region and the one or more second electrodes are in contact with the n-type region.

The first and second electrode may comprise any suitable electrically conductive material. The first electrode typically comprises a transparent conducting oxide. The second electrode typically comprises one or more metals. The second electrode may alternatively comprise graphite. Typically, the first electrode typically comprises a transparent conducting oxide and the second electrode typically comprises one or more metals.

The transparent conducting oxide may be as defined above and is often FTO, ITO, or AZO, and typically ITO. The metal may be any metal. Generally the second electrode comprises a metal selected from silver, gold, copper, aluminium, platinum, palladium, or tungsten. The electrodes may form a single layer or may be patterned.

A semiconductor device according to the invention, for instance a sensitized solar cell, may comprise the following layers in the following order:
- I. one or more first electrodes as defined herein;
- II. optionally a compact n-type layer as defined herein;
- III. a porous layer of an n-type material as defined herein;
- IV. a layer of said semiconducting material (e.g. as a sensitizer);
- V. a p-type region as defined herein;
- VI. optionally a further compact p-type layer as defined herein; and
- VII. one or more second electrodes as defined herein.

A semiconductor device according to the invention which is a photovoltaic device may comprise the following layers in the following order:
- I. one or more first electrodes as defined herein;
- II. an n-type region comprising at least one n-type layer as defined herein;
- III. a layer of the semiconducting material comprising the crystalline compound as defined herein;
- IV. a p-type region comprising at least one p-type layer as defined herein; and
- V. one or more second electrodes as defined herein.

A photovoltaic device according to the invention may comprise the following layers in the following order:
- I. one or more first electrodes which comprise a transparent conducting oxide, preferably FTO;
- II. an n-type region comprising at least one n-type layer as defined herein;
- III. a layer of the semiconducting material as defined herein;
- IV. a p-type region comprising at least one p-type layer as defined herein; and
- V. one or more second electrodes which comprise a metal, preferably silver or gold.

The one or more first electrodes may have a thickness of from 100 nm to 700 nm, for instance of from 100 nm to 400 nm. The one or more second electrodes may have a thickness of from 10 nm to 500 nm, for instance from 50 nm to 200 nm or from 10 nm to 50 nm. The n-type region may have a thickness of from 50 nm to 500 nm. The p-type region may have a thickness of from 50 nm to 500 nm.

In one embodiment, the semiconductor device may be a hole-transporter free photovoltaic device. For instance, the semiconductor device may not substantially comprise a layer of a p-type semiconductor. For example, in this embodiment, the semiconductor device does not comprise a layer of an organic p-type semiconductor. The semiconductor device may thus be a photovoltaic device, which photovoltaic device comprises:
an n-type region comprising at least one n-type layer;
a layer of an electrode material; and
disposed between the n-type region and the layer of an electrode material, a layer of the semiconducting material in contact with the layer of an electrode material.

The electrode material may be as described herein for the first or second electrode. For instance, the layer of the electrode material may be a layer of a transparent conducting oxide, a layer of a metal (such as gold) or a layer comprising graphite (for instance a carbon black/graphite composite).

The semiconductor device may be a mesoscopic photovoltaic device, for instance as described in Etgar, *Hole-transport material-free perovskite-based solar cells*, MRS Bulletin, Vol 40, August 2015. For instance, the semiconductor device may comprise:
a layer of a transparent conducting oxide (for instance FTO or ITO);
disposed on the layer of the transparent conducting oxide, a layer of an n-type metal oxide (for instance $TiO_2$ or $SnO_2$), which is optionally porous;
disposed on the layer of the n-type metal oxide, a layer of the crystalline compound as defined herein (for instance in Formula (III)); and
disposed on the layer of the crystalline compound, a layer of an electrode material (for instance a metal such as gold, or an electrode material comprising graphite).

The mesoscopic photovoltaic device may further comprise a porous layer of a dielectric material (for instance as described herein for the dielectric scaffold). This may be instead of the layer of the n-type metal oxide in the above structure. Alternatively, the mesoscopic device may comprise a porous layer of an n-type metal oxide (such as $TiO_2$) and a porous layer of a dielectric material (such as $ZrO_2$).

An example of a mesoscopic cell according to the invention may comprise:
a layer of a FTO or ITO;
optionally, disposed on the layer of FTO or ITO, a porous layer of $ZrO_2$;
disposed on the layer of FTO or ITO, or, if present, the porous layer of $ZrO_2$, a layer of $TiO_2$, which is optionally porous;
disposed on the layer of $TiO_2$, a layer of the crystalline compound as defined herein (for instance in Formula (III)); and
disposed on the layer of the crystalline compound, a layer of an electrode material comprising graphite.

The semiconductor device may be a tandem photovoltaic device and further comprises a layer of a second semiconductor material wherein the band gap of the second semiconductor material is lower than the band gap of the semiconductor material comprising the crystalline compound. Thus, the second semiconductor material and the semiconductor material comprising the crystalline compound may have different absorption profiles and absorb different parts of the solar spectrum.

The second semiconductor material may for instance comprise silicon, a perovskite, copper indium selenide (CIS), copper indium gallium diselenide (CIGS), CdTe, PbS or PbSe. Preferably, the second semiconductor material comprises silicon or a perovskite. The perovskite may be a perovskite of formula $[A][B][Y]_3$ with [A] as one or more monocations (for instance Cs', $NH_3CH_3$' or $(H_2N-C(H)$=$NH_2)$'), [B] as one or more metal or metalloid dications (as defined herein, e.g. $Pb^{2+}$) and [Y] as one or more halide anions. For instance, the perovskite may be $(NH_3CH_3)PbI_3$. More preferably, the second semiconductor material comprises silicon. The silicon is typically crystalline silicon, and may be intrinsic silicon (i-Si), n-type silicon (n-Si) or p-type silicon (p-Si).

The tandem photovoltaic device typically comprises:
(i) a layer of silicon;
(ii) disposed on the layer of silicon, a layer of a transparent conducting oxide;
(iii) disposed on the layer of a transparent conducting oxide, an n-type region comprising at least one n-type layer;
(iv) disposed on the n-type region, a layer of said semiconducting material;
(v) disposed on the layer of said semiconducting material, a p-type region comprising at least one p-type layer; and
(vi) disposed on the p-type region, a layer of an electrode material.

The invention also provides a process for producing a layer of a crystalline compound, which crystalline compound comprises: (i) Cs'; (ii) $(H_2N-C(H)$=$NH_2)$'; (iii) one or more metal or metalloid dications [B]; and (iv) a first halide anion X; and (v) a second halide anion X', which process comprises:
(a) disposing on a substrate a precursor composition comprising:
CsX and/or CsX';
$(H_2N-C(H)$=$NH_2)X$ and/or $(H_2N-C(H)$=$NH_2)X'$;
$BX_2$ and/or $BX'_2$.

The components of the precursor composition may be disposed on the substrate (simultaneously or separately) by vapour deposition. Disposing on a substrate a precursor composition may therefore comprise:
(Ai) exposing the substrate to one or more vapours, which one or more vapours comprise said precursor composition; and
(Aii) allowing deposition of the one or more vapours onto the substrate to produce a layer of the crystalline compound thereon.

The components of the precursor composition may be disposed on the substrate (simultaneously or separately) by solution deposition. Disposing on a substrate a precursor composition may therefore comprise:
(Bi) disposing the precursor composition and one or more solvents on the substrate; and
(Bii) removing the one or more solvents to produce on the substrate a layer of crystalline compound.

In the process of the invention, the crystalline compound may be as further defined herein. Preferably, the precursor composition comprises:
CsI and/or CsBr;
$(H_2N-C(H)$=$NH_2)I$ and/or $(H_2N-C(H)$=$NH_2)Br$;
$PbI_2$;
$PbBr_2$; and
a polar aprotic solvent.

Examples of polar aprotic solvents include dimethylformamide (DMF), acetonitrile and dimethylsulfoxide (DMSO).

For instance, the process of the invention may comprise disposing on a substrate a composition comprising: dimethylformamide (as a solvent); CsI and/or CsBr; $(H_2N-C(H)$=$NH_2)I$ and/or $(H_2N-C(H)$=$NH_2)Br$; $PbI_2$; and $PbBr_2$; and removing the solvent. The composition may be disposed on the substrate by spin coating.

Removing the one or more solvents typically comprises heating the one or more solvents or allowing the one or more solvents to evaporate. The substrate, solvent or first region may be heated at a temperature of from 40° C. to 100° C. for a time of from 5 minutes to 2 hours to remove the one or more solvents.

The substrate may be any suitable substrate. Typically the substrate comprises a layer of an electrode material and a layer of an n-type semiconductor, for instance a compact layer of $SnO_2$ or $TiO_2$.

The invention also provides a process for producing a semiconductor device, which process comprises a process for producing a layer of a crystalline compound as defined herein. The semiconductor device produced may be as further defined herein.

After the layer of the crystalline compound is deposited, the process may further comprise a step of annealing the layer of the crystalline compound. For instance, the layer of the crystalline compound may be heated to a temperature of from 50° C. to 200° C. or from 70° C. to 150° C. The second region may be heated to a temperature of from 90° C. to 110° C. The layer of the crystalline compound may be heated for a time from 30 seconds to 60 minutes, for instance from 2 minutes to 25 minutes.

Typically, the process further comprises disposing a third region on the layer of the crystalline compound, wherein: said third region is a p-type region comprising at least one p-type layer; or said third region is an n-type region comprising at least one n-type layer.

The third region is typically a p-type region comprising at least one p-type layer, preferably wherein the at least one p-type layer comprises an organic p-type semiconductor. The p-type region may be as described above.

The third region is typically disposed on the layer of the crystalline compound until it has a thickness of from 50 nm to 1000 nm, for instance 100 nm to 500 nm. Disposing the third region on the layer of the crystalline compound typically comprises disposing a composition comprising a p-type material and a solvent on the layer of the crystalline compound (for instance by spin-coating) and removing the solvent. The p-type material may be any p-type material described herein. Preferably, said third region is a p-type region comprising at least one p-type layer, preferably wherein the at least one p-type layer comprises an organic p-type material, for instance spiro-OMeTAD.

The process typically further comprises: disposing one or more second electrodes on the third region. The one or more second electrodes may be as defined above for an semiconductor device according to the invention. For instance, the second electrodes may comprise a metal such as silver. The one or more second electrodes are typically disposed by vacuum vapour deposition, for instance by evaporation at a low pressure (e.g less than or equal to $10^{-5}$ mbar) optionally through a shadow mask.

The invention is now described in more detail with reference to the following Examples.

EXAMPLES

Example 1—Synthesis of Devices Contain (FA/Cs)Pb(I/Br)$_3$ Perovskites

Materials and Methods:
Materials:
Unless otherwise stated, all materials were purchased from Sigma-Aldrich or Alfa Aesar and used as received. Spiro-OMeTAD was purchased from Borun Chemicals and used as received.

Perovskite Precursor Synthesis:
Formamidinium iodide (FAI) and formamidinium bromide (FABr) were synthesised by dissolving formamidinium acetate powder in a 1.5× molar excess of 57% w/w hydroiodic acid (HI), or 48% w/w hydrobromic acid (for FABr). After addition of acid the solution was left stirring for 10 minutes at 50° C. Upon drying at 100° C. for 2 h, a yellow-white powder is formed. This was then washed three times with diethyl ether. The power was later dissolved in ethanol heated at 80° C. to obtain a supersaturate solution. Once fully dissolved, the solution is then placed in a refrigerator for overnight recrystallization. The recrystallization process forms white needle-like crystals. The powder is later washed with diethyl ether three times. Finally, the powder is dried overnight in a vacuum oven at 50° C.

Perovskite Precursor Solution Mixture:
For XRD and optical measurements, two series of films ranging from neat I to neat Br were formed; one with FA as the only cation and one with 83% FA and 17% Cs. To form each specific composition ranging from neat Br to neat I, two separate precursor solutions were made: $FAPbI_3$ and $FAPbBr_3$, for the FA series. Two additional precursor solutions were made: $FA_{0.83}Cs_{0.17}PbI_3$ and $FA_{0.83}Cs_{0.17}PbBr_3$, for the FA/Cs series. All solutions were dissolved in anhydrous N,N-dimethylformamide (DMF) to obtain a stoichiometric solution with desired composition using precursor salts: FAI, FABr, CsI, CsBr, $PbI_2$, $PbBr_2$, 31.7 µl of 57% w/w hydroiodic acid (HI) and 18.8 µl of 48% w/w hydrobromic acid (HBr) were added to 1 ml of 0.55M precursor solutions for both solutions. To form the $FA_{0.83}Cs_{0.17}Pb(I_{0.6}Br_{0.4})_3$ "optimized precursor solution composition" used for the device fabrication, FAI, CsI, $PbBr_2$ and $PbI_2$ were dissolved in DMF to obtain a stoichiometric solution with desired composition and a molar concentration of 0.95M, 54.7 µl of HI and 27.3 µl of HBr was added to 1 ml of 0.95M precursor solutions. After the addition of the acids, the solution was stirred for 72 hours under a nitrogen atmosphere.

Perovskite Solar Cell Fabrication:
The precursor perovskite solution was spin-coated in a nitrogen-filled glovebox at 2000 rpm for 45 s, on a substrate pre-heated at 70° C. The films were dried inside a N2 glovebox on a hot plate at a temperature of 70° C. for 1 minute. The films were then annealed in an oven in an air atmosphere at 185° C. for 90 minutes.

Hole-Transporting Layer Fabrication:
The electron-blocking layer was deposited with a 96 mg/ml of 2,2',7,7'-tetrakis-(N,N-di-p-methoxyphenylamine) 9,9'-spirobifluorene (spiro-OMeTAD) solution in chlorobenzene. Additives of 32 µl of lithium bis(trifluoromethanesulfonyl)imide (170 mg/ml 1-butanol solution) per 1 ml of spiro-OMeTAD solution and 10 ul of 4-tert-butylpyridine per 1 ml of spiro-OMeTAD solution. Spin-coating was carried out in a nitrogen-filled glovebox at 2000 rpm for 60 s.

Electrode:
A 120 nm silver electrode was thermally evaporated under vacuum of $\approx 10^{-6}$ Torr, at a rate of $\approx 0.2$ nm·s$^{-1}$.

Device Characterization:
The current density-voltage (J-V) curves were measured (2400 Series SourceMeter, Keithley Instruments) under simulated AM 1.5 sunlight at 100 mWcm$^{-2}$ irradiance generated by an Abet Class AAB sun 2000 simulator, with the intensity calibrated with an NREL calibrated KG5 filtered Si reference cell. The mismatch factor was calculated to be less than 1%. The active area of the solar cell is 0.0919 cm. The forward J-V scans were measured from forward bias (FB) to short circuit (SC) and the backward scans were from short circuit to forward bias, both at a scan rate of 0.38V s$^{-1}$. A stabilization time of 5 s at forward bias of 1.4 V under illumination was done prior to scanning. The EQE was measured using Fourier transform photocurrent spectroscopy. The EQE was measured in short-circuit ($J_{SC}$) configuration following a 1.4V prebias for 20 s, using a simulated air-mass (AM) 1.5 100 mW cm-2 sun light as illumination source.

Substrate Preparation:

Devices were fabricated on fluorine-doped tin oxide (FTO) coated glass (Pilkington, 7Ω☐$^{-1}$). Initially, FTO was removed at specific regions where the anode contact will be deposited. This FTO etching was done using a 2M HCl and zinc powder. Substrates were then cleaned sequentially in hallmanex detergent, acetone, isopropyl alcohol. The FTO was then cleaned for 10 minutes using oxygen plasma. A hole-blocking layer was formed by immersing the cleaned FTO substrate in a bath of 40 mM SnCl$_4$ for 30 minutes at 80° C. The substrates were rinsed in two consecutive deionized water baths and then sonicated for 10 s in an ethanol bath. The substrates were then dried with a nitrogen gun. A 7.5 mg/ml of Phenyl-C60-butyric acid methyl ester (PCBM) solution in chlorobenzene was then spin coated onto the SnO$_2$ compact layer at 2000 rpm for 45 seconds and annealed at 70° C. for 10 minutes inside a N2 glove box.

Optical Pump-THz Probe Spectroscopy:

The optical-pump-THz-probe setup uses a Spectra Physics Ti:Sapphire regenerative amplifier to generate 40 's pulses at a center wavelength of 800 nm and a repetition rate of 1.1 kHz. Terahertz pulses were generated by optical rectification in a 450 μm thick GaP(110) single crystal and detected by electro-optic sampling in a ZnTe crystal (0.2 mm (110)-ZnTe on 3 mm (100)-ZnTe). Pulses for optical excitation of the samples at 400 nm have been generated using a beta barium borat frequency doubling crystal. Optical excitation was carried out from the substrate side of the film. The diameters of optical pump and THz probe beams at the sample position were 3.6 mm and 2.4 mm (FWHM), respectively. Measurements were performed with the entire THz beam path (including emitter, detector and sample) in an evacuated chamber at a pressure of <10$^{-2}$ bar.

Solar Cell Fabrication:

The experimental details on the silicon cell fabrication can be found elsewhere.(33) Briefly, both-side random pyramid textured float zone n-type <100> oriented wafers with 4 inch diameter, ~250 μm thickness, and a resistivity of 2-5 Ω·cm were used. The wafers were cleaned using the standard RCA process and the resulting oxides were removed by dipping in diluted hydrofluoric acid immediately before a-Si:H deposition. Intrinsic a-Si:H layers were deposited by standard PECVD processes using silane, SiH4, as precursor gas. The n-type and p-type doped a-Si:H layers were prepared by adding PH3 or B2H6 to the precursor gas, respectively. On the front side of the wafer, 80 nm ITO was deposited by RF magnetron sputter deposition from a ceramic target at room temperature. The back contact was formed by sputtering 80 nm of aluminum doped zinc oxide (AZO) and 200 nm silver in a Leybold Optics A600V7 tool. The front side contact grid consists of a stack of 10 nm Ti and 1500 nm Ag, thermally evaporated through a shadow mask. Following this fabrication process, the cells were annealed at 160° C. for 70 min in air.

Transparent Electrode:

A thin layer of ITO (Indium Tin Oxide) nanoparticles (<100 nm), from ITO dispersion in isopropanol, was spin coated on hole transport layer as the buffer layer to protect the spiro-OMeTAD during ITO sputtering. Then a ~120-nm thick layer of ITO was sputter coated on the buffer layer using a PVD 75 Kurt J. Lesker.

Results and Discussion

By the above method, a highly crystalline material was produced with complete tunability of the band gap around 1.75 eV, and charge mobility, recombination dynamics and low electronic disorder comparable to those of neat lead triiodide perovskites were observed. High efficiency solution-processed planar heterojunction solar cells were fabricated which demonstrated PCEs of over 17% and stabilized power outputs (SPO) of 16%. To demonstrate the potential impact of this new perovskite material in tandem solar cells, an indium tin oxide (ITO) top electrode was included to create a semi-transparent perovskite solar cell, the performance of a silicon cell was measured after "filtering" the sun light through the perovskite top cell. The silicon cells delivered an efficiency boost of 7.3% measured on the rear side of a semi-transparent perovskite cell, indicating the feasibility for achieving greater than 25% efficient perovskite-silicon tandem cells.

Figure 2:
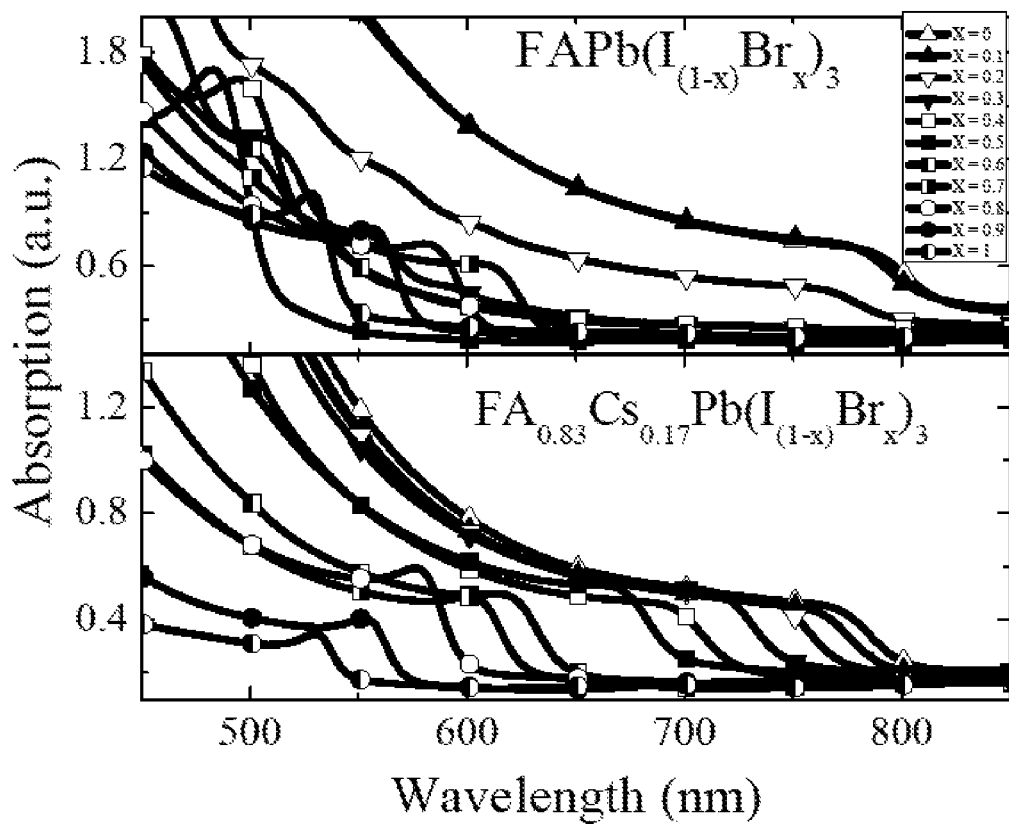
FIG. 2 shows (top) UV-Vis absorbance spectra of perovskite films for the $FAPb(I_{(1-x)}Br_x)_3$ system and (bottom) for the $FA_{0.83}Cs_{0.17}Pb(I_{(1-x)}Br_x)_3$ system.

In the 3D perovskite structure ABX$_3$, the A-site cations which could be employed with lead halides to form suitable perovskites for solar cell applications are typically Cs, MA and FA. CsPbI$_3$ does form a "black phase" perovskite with a band gap of 1.73 eV, however, this appropriate phase is only stable at temperatures above 200 to 300° C. and the most stable phase at room temperature is a non-perovskite orthorhombic "yellow" phase, rendering it less useful. MA based perovskites are thermally unstable and suffer from halide segregation instabilities, and are thus likely to be unsuitable. FA based perovskites are the most likely to deliver the best balance between structural and thermal stability. However, in FIG. 1A are shown photographs of a series of FAPb(I$_{(1-x)}$Br$_x$)$_3$ films ranging from neat Br to neat I; a "yellowing" of the films is observed for compositions between x=0.3 and x=0.6 of the FAPb(I$_{(1-x)}$Br$_x$)$_3$ system, consistent with the previously reported phase instability due to a transition from a trigonal (x<0.3) to cubic (x>0.5) structures. It has previously been observed that the band gap changes from 1.48 eV for FAPbI$_3$ to 1.73 eV for CsPbI$_3$. The inventors therefore considered the possibility that if we partially substitute FA for Cs, we may be able to push this region of structural instability to higher energies, and thus achieve a structurally stable mixed halide perovskite with a band gap of 1.75 eV. In FIG. 1B are shown photographs of thin films fabricated from mixed-cation lead mixed-halide FA$_{0.83}$Cs$_{0.17}$Pb(I$_{(1-x)}$Br$_x$)$_3$ compositions. Unexpectedly, the region of structural instability is not simply shifted to higher energy, but a continuous series of dark films is observed throughout this entire Br to 1 compositional range. To confirm these observations, also performed were UV-vis absorption measurements. As shown in FIG. 2 (top) and (bottom), a sharp optical band edge for all Br—I compositions of the mixed-cation FA$_{0.83}$Cs$_{0.17}$Pb(I$_{(1-x)}$Br$_x$)$_3$ perovskite material were obtained, in contrast to FAPb(I$_{(1-x)}$Br$_x$)$_3$ which shows weak absorption in the intermediate range.

Figure 3:
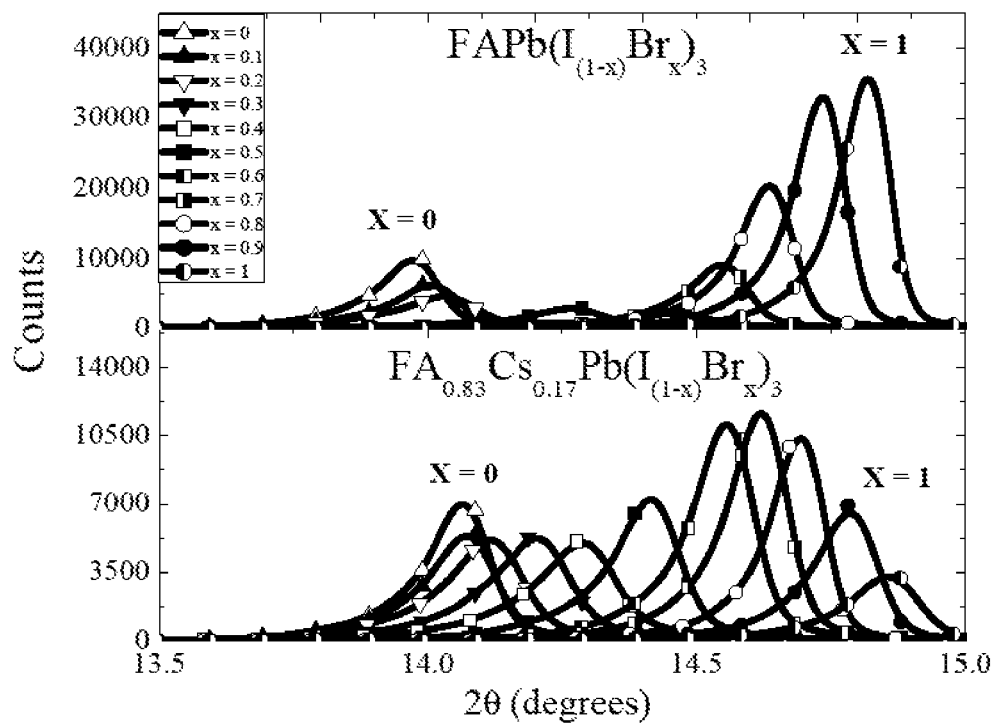
FIG. 3 shows (top) the x-ray diffraction (XRD) pattern of $FAPb(I_{(1-x)}Br_x)_3$ perovskites and (bottom) of the $FA_{0.83}Cs_{0.17}Pb(I_{(1-x)}Br_x)_3$ system.
Figure 12:
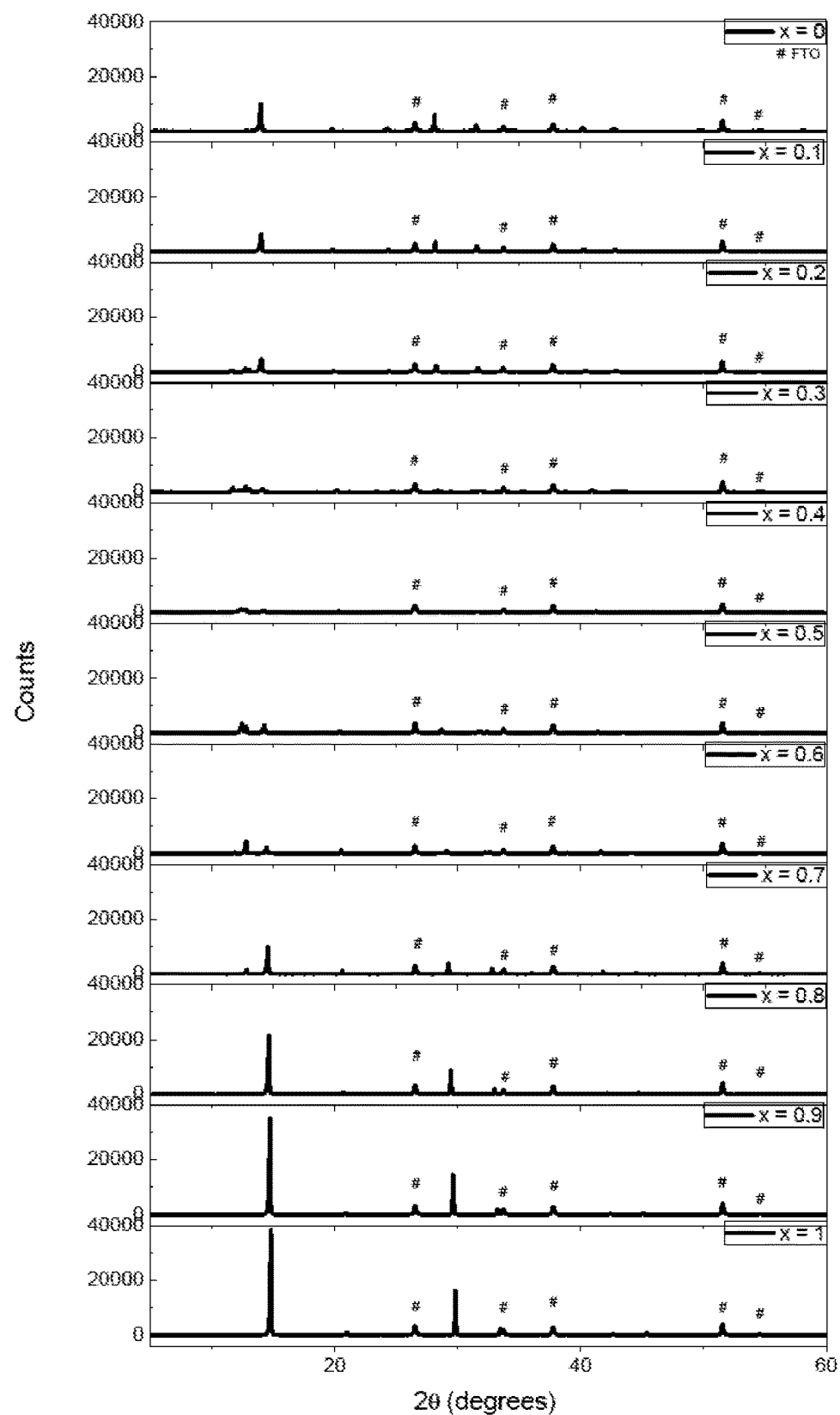
FIG. 12 shows x-ray diffraction pattern (XRD) for the entire range of $FAPb(I_{(1-x)}Br_{(x)})_3$ perovskites formed on fluorine-doped tin oxide (FTO) coated glass substrates. Peaks labelled with # are assigned to the FTO substrate.
Figure 13:
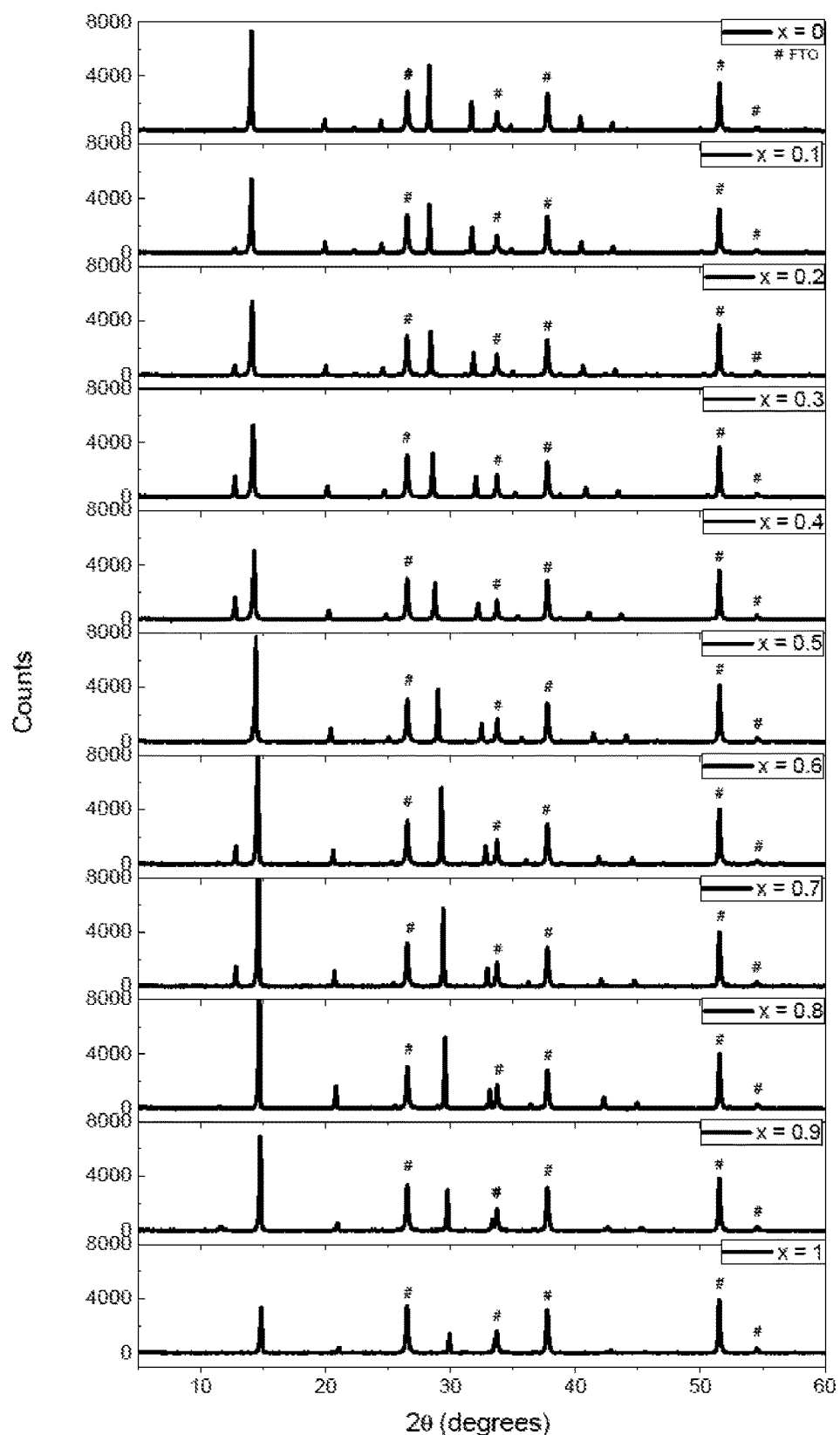
FIG. 13 shows x-ray diffraction pattern (XRD) for the entire range of $FA_{0.83}Cs_{0.17}Pb(I_{(1-x)}Br_{(x)})_3$ perovskites formed on fluorine-doped tin oxide (FTO) coated glass substrates. Peaks labelled with # are assigned to the FTO substrate.
Figure 14:
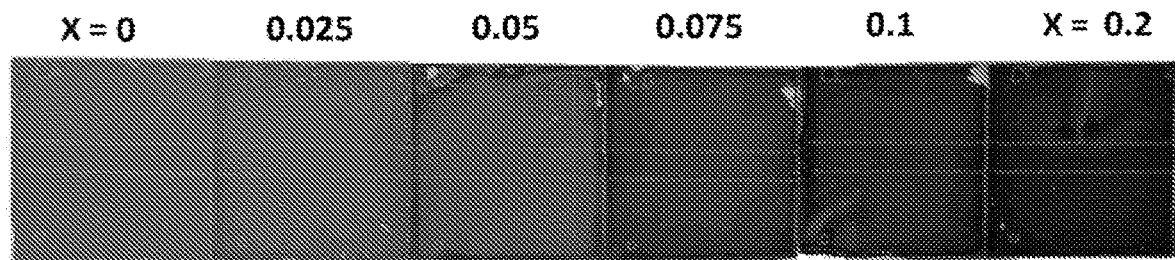
FIG. 14 show s a photograph of perovskite films with a Cs composition increasing from x=0 to 0.2.
Figure 15:
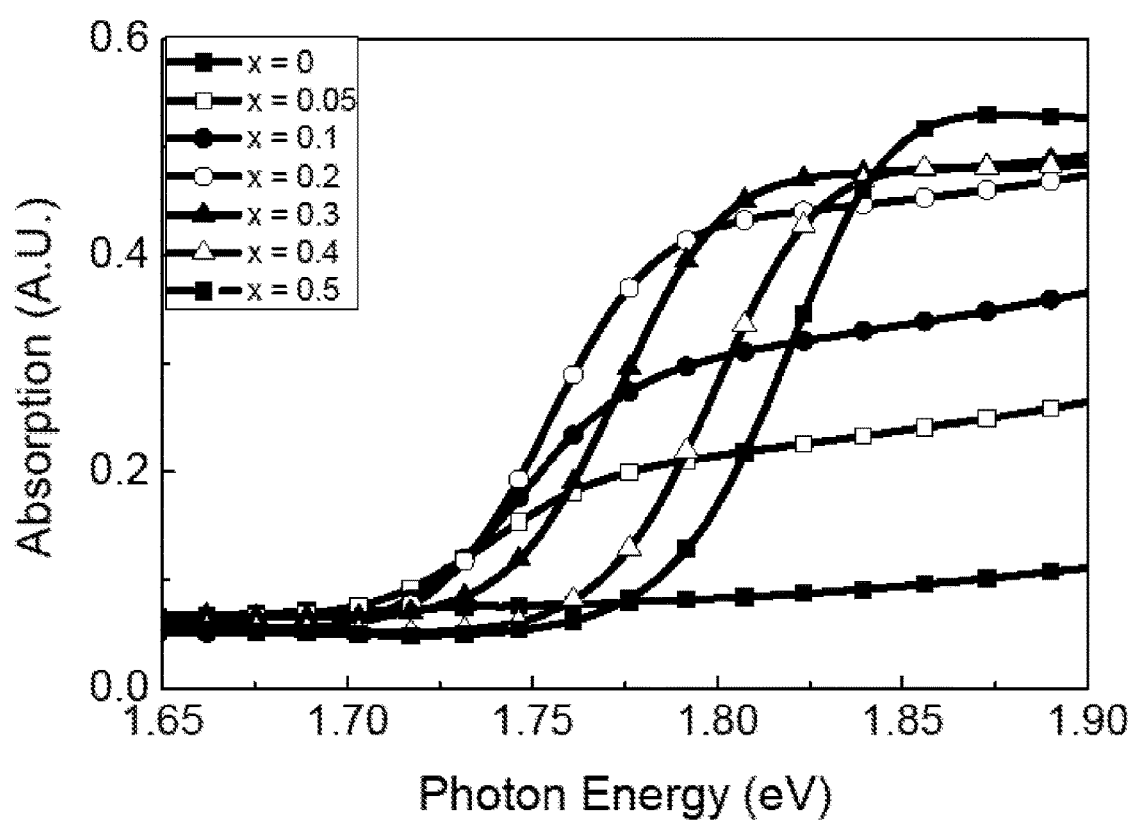
FIG. 15 shows the U V-Vis absorbance of perovskite films where the ratio x of Cs is varied from 0 to 0.5.
Figure 16:
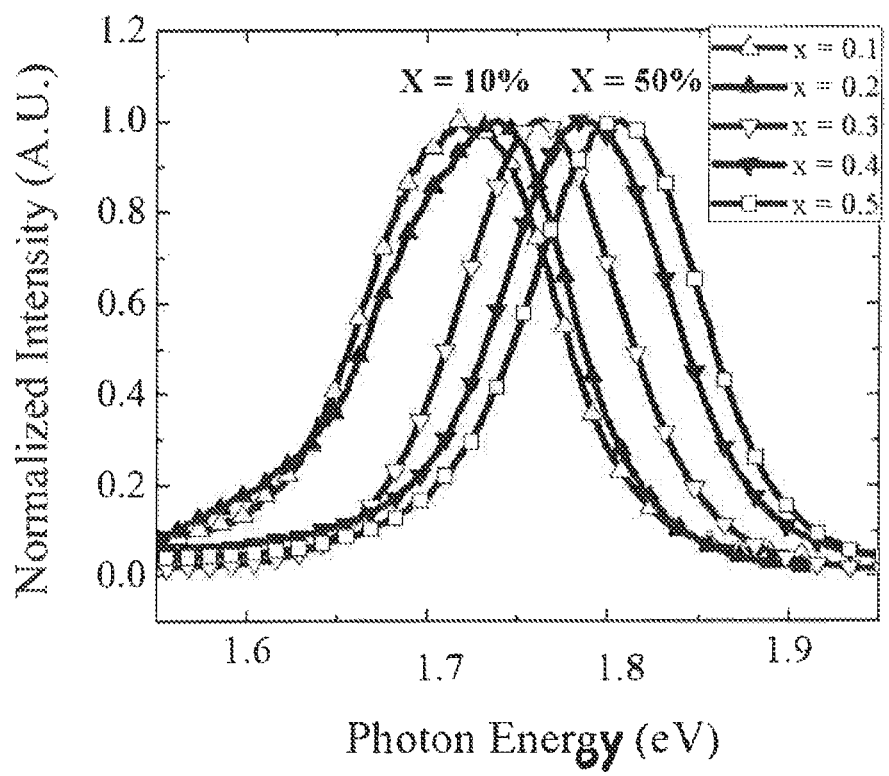
FIG. 16 shows stead)-state photoluminescence spectra for perovskites having a Cs content varying from x=0.1 to 0.5.
Figure 17:
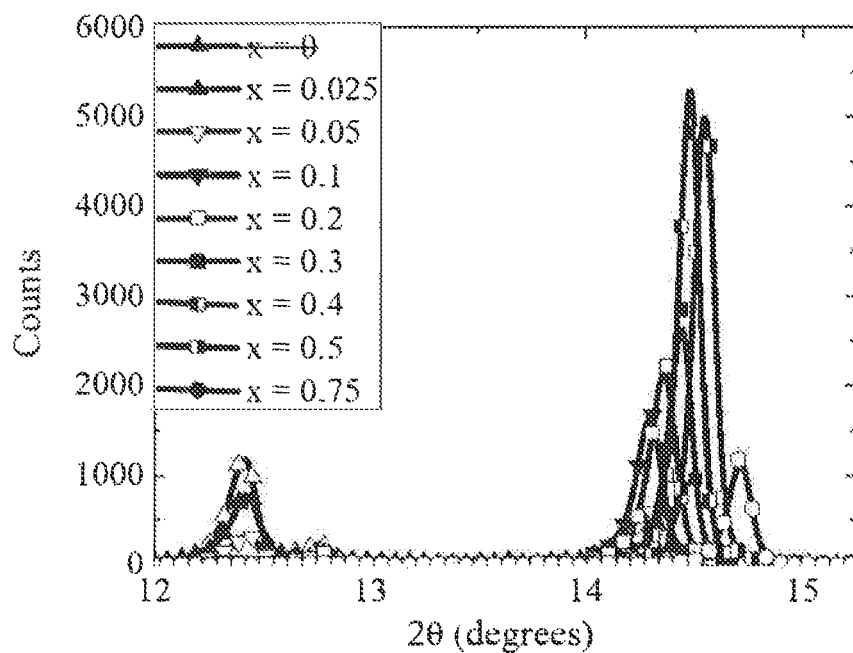
FIG. 17 shows x-ray diffraction (XRD) pattern of perovskite material showing the formation of a single crystalline (100) cubic peak and its shift with increasing Cs content from x=0 to 0.75.
Figure 18:
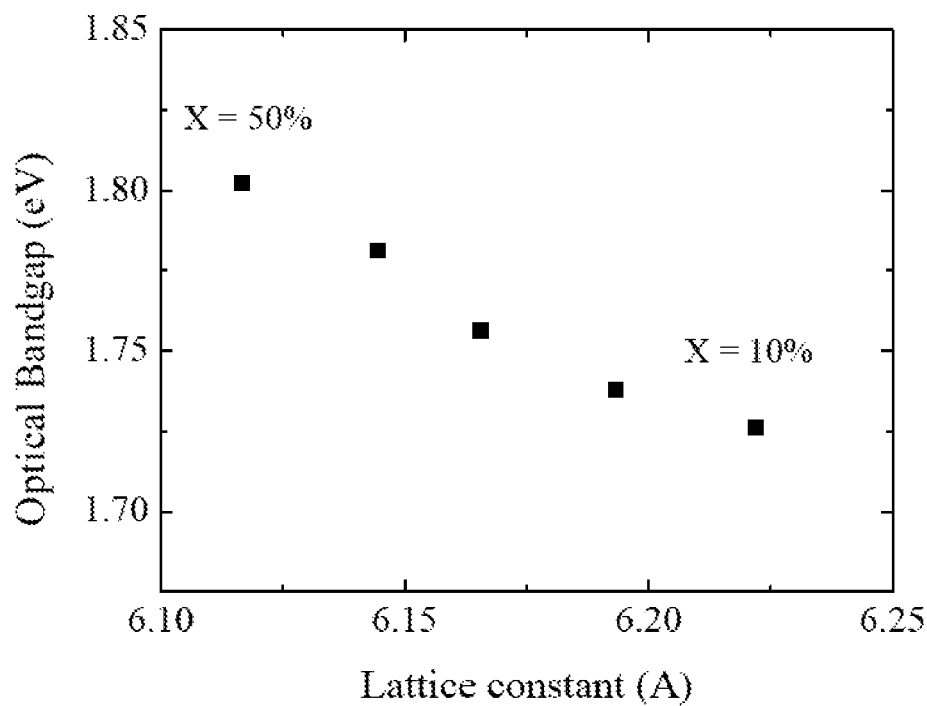
FIG. 18 shows the variation in band gap with cubic lattice parameter as determined from XRD pattern and a Tauc plot as the Cs content x varies from 0.1 to 0.5.
Figure 19:
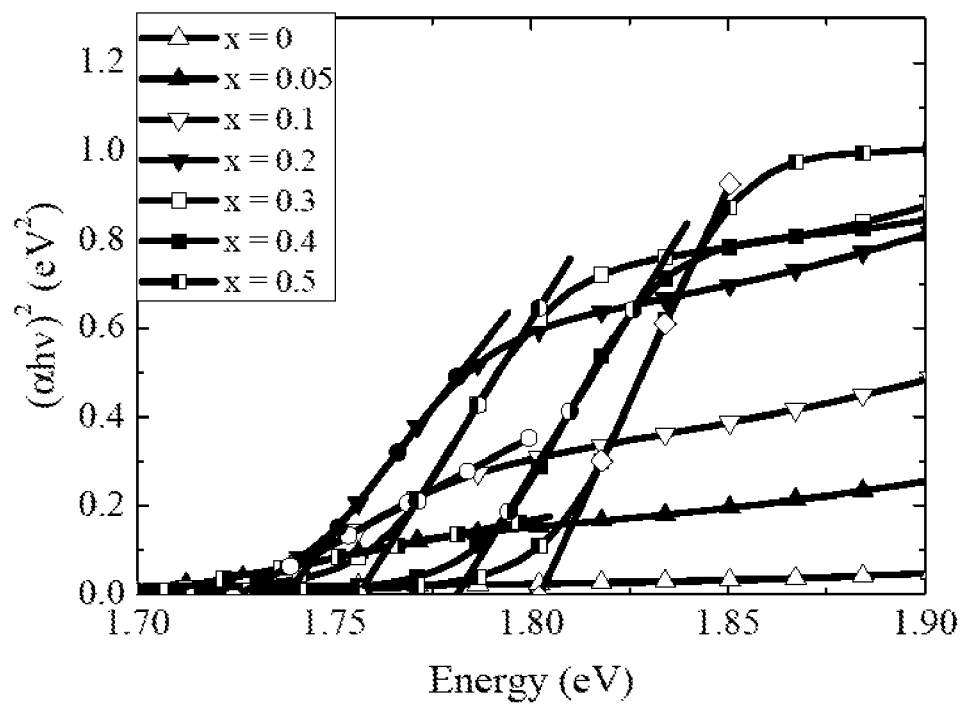
FIG. 19 shows a Tauc plot of $FA_{(1-x)}Cs_xPb(I_{0.6}Br_{0.4})_3$ as the Cs content x varies from 0 to 0.5 assuming direct band gap and showing determination of estimated band gap from intercept.
Figure 20:
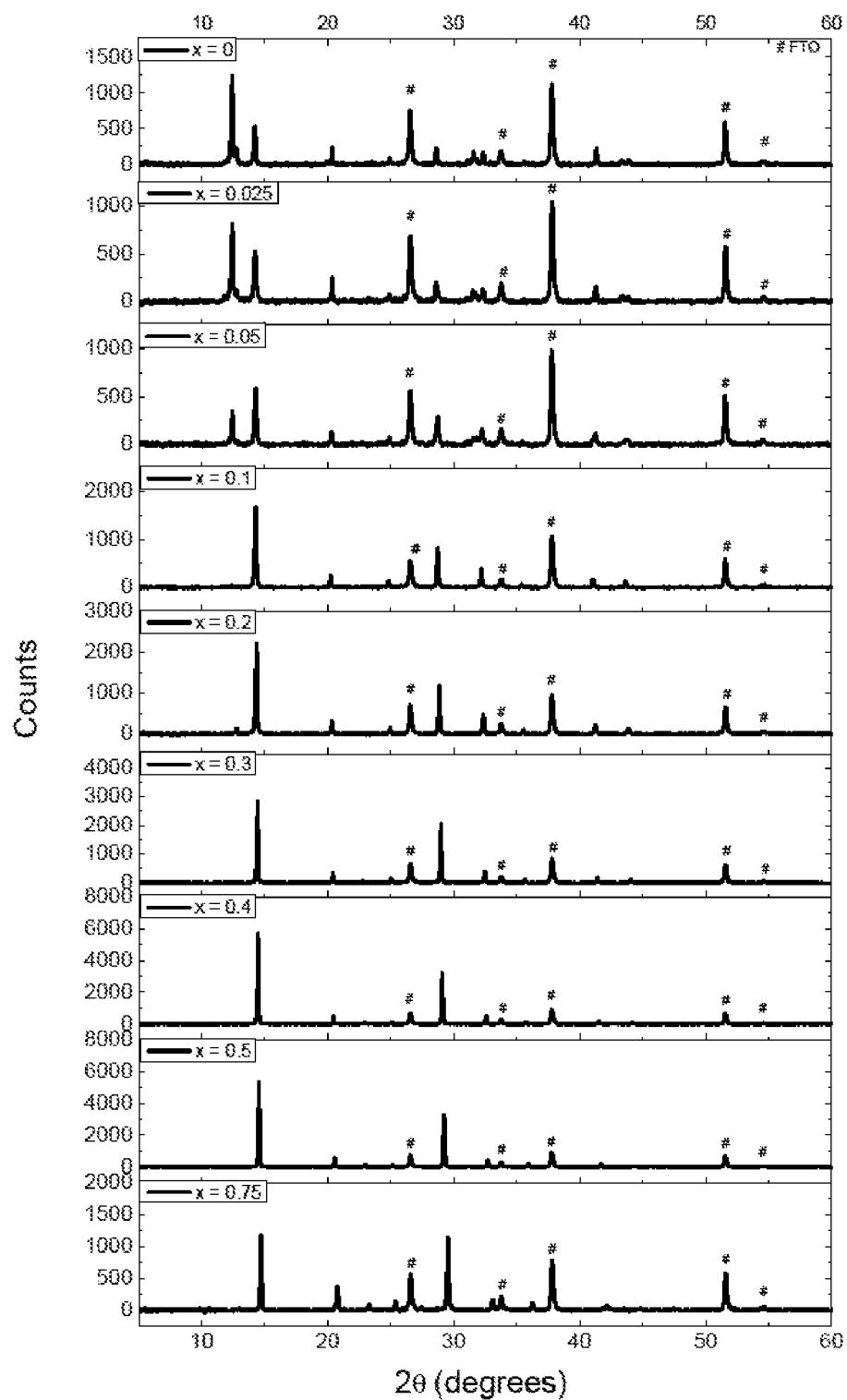
FIG. 20 shows the x-ray diffraction pattern (XRD) for the full range of $FA_{(1-x)}Cs_{(x)}Pb(I_{0.6}Br_{0.4})_3$ perovskites formed on fluorine-doped tin oxide (FTO) coated glass substrates when annealed at 170° C. for 10 minutes, using a 0.55M solution. Peaks labelled with # are assigned to the FTO substrate.
Figure 21:
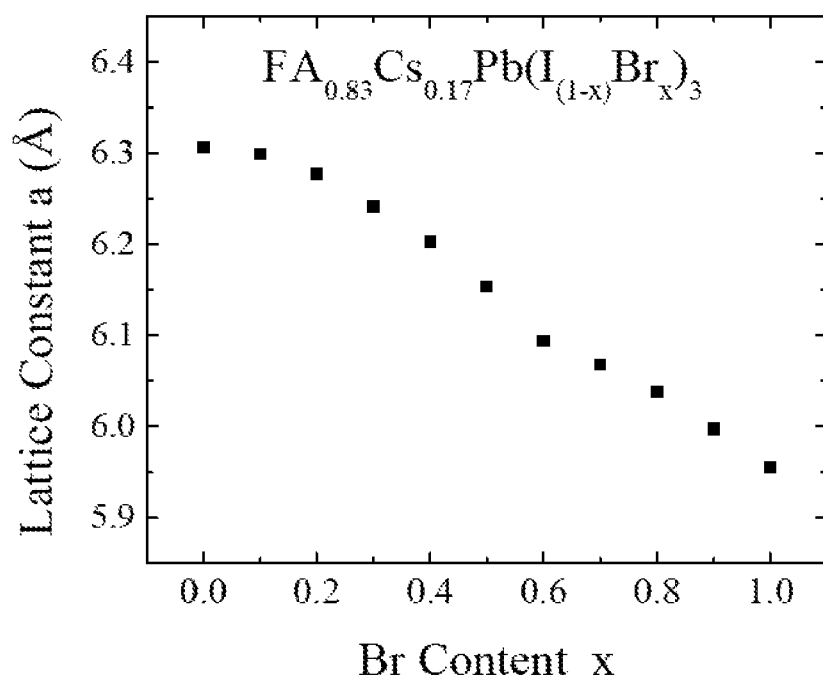
FIG. 21 shows the lattice constant of $FA_{0.83}Cs_{0.17}Pb(I_{(1-x)}Br_{(x)})_3$ perovskite system plotted as a function of bromide content. This linear relationship between lattice constant and bromide content indicates that this system follows Vegard's law

In order to understand the impact of adding caesium upon the crystallization of the perovskite in more detail, X-ray diffraction (XRD) studies were performed on the series of films covering the I to Br compositional range. In FIG. 3 (top) is shown the XRD patters for FAPb(I$_{(1-x)}$Br$_x$)$_3$, zoomed in on the peak around 2θ~14°. FAPb(I$_{(1-x)}$Br$_{(x)}$)$_3$ perovskites were formed on fluorine-doped tin oxide (FTO) coated glass substrates when annealed at 170° C. for 10 m, using a 0.55M solution. The complete diffraction pattern is shown in FIG. 12. FAPb(I$_{(1-x)}$Br$_x$)$_3$ undergoes a structural phase transition from a trigonal phase for x<0.3 into a cubic phase for x>0.5, with structural instability in the intermediate region. Quite remarkably, for the $FA_{0.83}Cs_{0.17}Pb(I_{(1-x)}Br_x)_3$ the material is in a single phase throughout the entire compositional range (see FIG. 1F). The monotonic shift of the (100) reflection which we observe from 2θ~14.2° to 14.9° is consistent with a cubic lattice constant shift from 6.306 Å to 5.955 Å as the material incorporates a larger fraction of the smaller halide, Br. The complete diffraction pattern is shown in FIG. 13. Therefore, it can be confidently stated that for the $FA_{0.83}Cs_{0.17}Pb(I_{(1-x)}Br_x)_3$ perovskite, the structural phase transition has been removed and stability is now present over the entire compositional range. The impact of varying the Cs concentration and the Br to I concentration are shown in FIGS. 14 to 20. Quite remarkably over the entire Br to I range, and for a large fraction of the Cs-FA range the variation in lattice constant, composition and band gap precisely follow Vegard's law, as shown in FIG. 21. This indicates a total flexibility and predictability in tuning of the composition and its impact upon the band gap. For the remainder of Example 1, the precise composition $FA_{0.83}Cs_{0.17}Pb(I_{0.6}Br_{0.4})_3$ which has a band gap of 1.74 eV (FIG. 22) is used unless stated otherwise.

Figure 4:
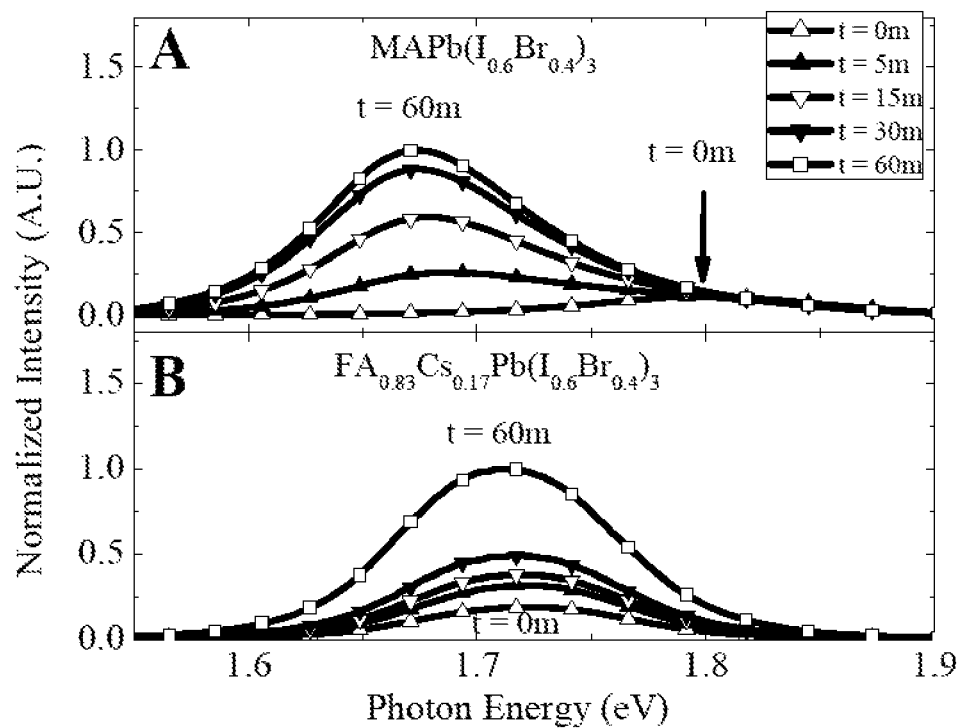
FIG. 4 shows (A) normalized photoluminescence (PL) measurement of the $MAPb(I_{0.6}Br_{0.4})_3$ thin film, measured after 0, 5, 15, 30 and 60 minutes of light exposure using a power density of ~3 mW cm$^{-2}$ and a wavelength of 550 nm as excitation source and (B) PL Measurement of the $FA_{0.83}Cs_{0.17}Pb(I_{0.6}Br_{0.4})_3$ thin film exposed to identical light illumination conditions.
Figure 23:
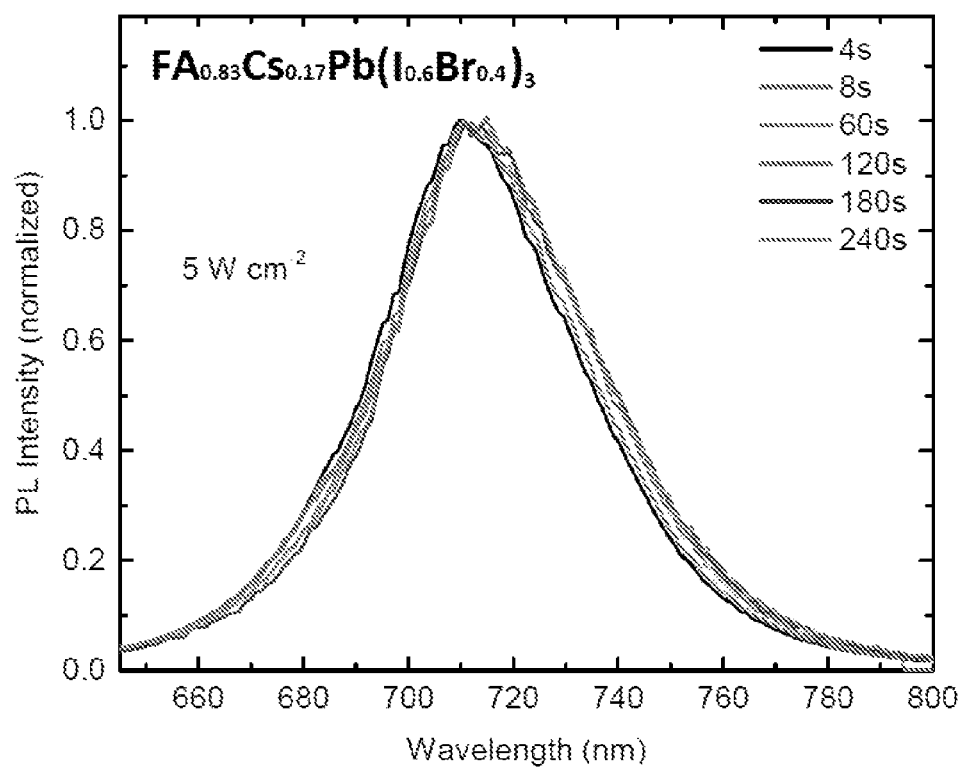
FIG. 23 shows photoluminescence spectra of $FA_{0.83}Cs_{0.17}Pb(I_{0.6}Br_{0.4})_3$ following excitation with pulse fluence of 0.5 μJcm$^{-2}$ and laser intensity of 5 Wcm$^{-2}$ at a wavelength of 405 nm.

Photo-induced halide segregation has been reported in methylammonium lead mixed-halide perovskites. A red-shift in PL upon light illumination, with intensities ranging from 10-100 mW cm$^{-2}$ occurs, with the shift to lower energies resulting from the formation of iodine rich domains which have lower band gaps. This limits the achievable open-circuit voltage of the solar cell device by introducing a large degree of electronic disorder. In FIGS. 4A and 4B the photoluminescence from films of $MAPb(I_{0.6}Br_{0.4})_3$ perovskite and the mixed cation mixed halide material $FA_{0.83}Cs_{0.17}Pb(I_{0.6}Br_{0.4})_3$ are shown. The PL from both films was measured immediately after prolonged periods of light exposure, using a power density of ~β mW cm$^{-2}$ and a wavelength of 550 nm as excitation source. The halide segregation results observed by Hoke et al. were confirmed where we see a significant time-dependent red-shift in PL for the $MAPb(I_{0.6}Br_{0.4})_3$ film, which exhibits a 130 meV PL red-shift after only 1 hour of illumination. However, although a rise in PL intensity is seen, no significant red-shift in PL emission for the $FA_{0.83}Cs_{0.17}Pb(I_{0.6}Br_{0.4})_3$ precursor composition is observed after 1 hour of identical light illumination (which is show n in FIG. 5). Furthermore, as shown in FIG. 23, we also exposed a similar $FA_{0.83}Cs_{0.17}Pb(I_{0.6}Br_{0.4})_3$ film to monochromatic irradiance of much higher 5 Wcm$^{-2}$ irradiance, and observe no red shift after 240 seconds of illumination. Under these identical conditions, a red shift is observed in the PL for the single cation $FAPb(I_{0.6}Br_{0.4})$ perovskite.

Figure 5:
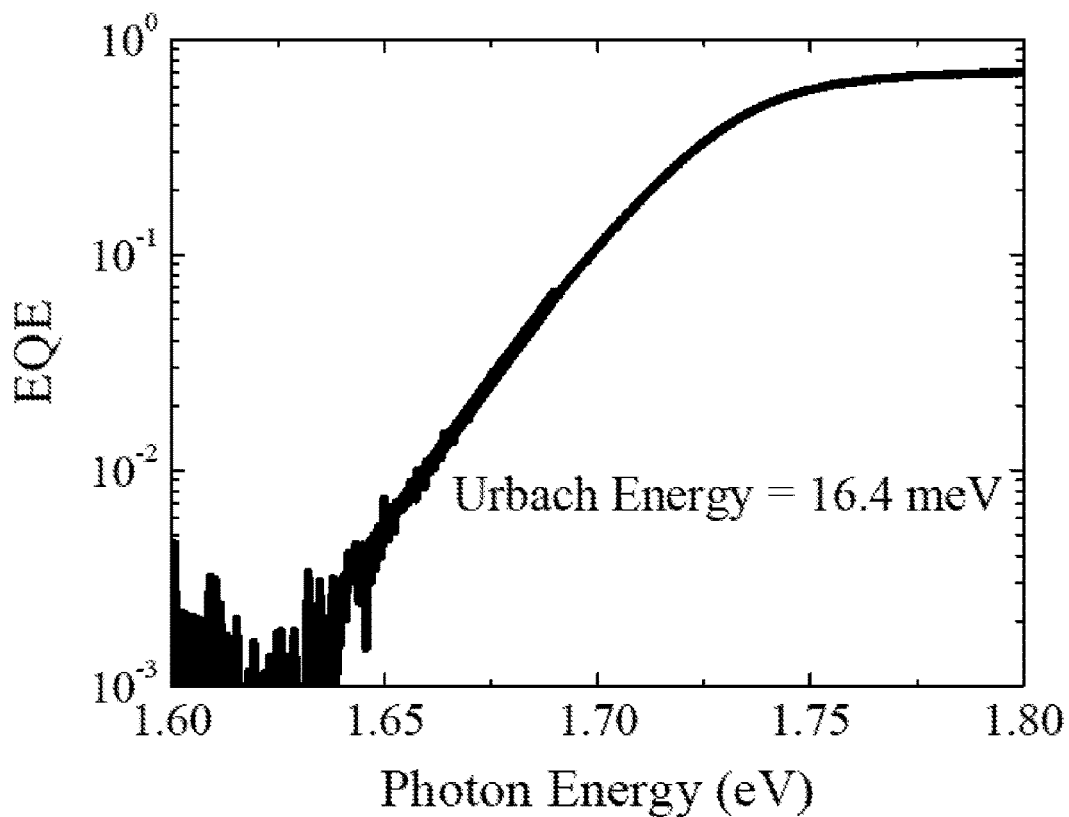
FIG. 5 shows a semi-log plot of external quantum efficiency (EQE) at the absorption onset for the same sample as FIG. 4, measured using FTPS in short-circuit (Jsc) configuration.

Beyond halide segregation, a further deleterious observation previously made for mixed halide perovskites has been that the energetic disorder in the material is greatly increased in comparison to the neat iodide perovskites. The ultimate open-circuit voltage a solar cell material can generate is intimately linked to the steepness of the absorption onset just below the band edge, which can be quantified by a term known as the Urbach energy ($E_u$). This $E_u$ reported for $MAPbI_3$ was 15 meV, where small values of E indicate low levels of electronic disorder. In contrast, the $E_u$ for $MAPb(I_{0.6}Br_{0.4})_3$ perovskite increases to 49.5 meV which represents similar levels of electronic disorder as organic photovoltaics and amorphous silicon. In order to determine the Urbach energy for the present system. Fourier transform photocurrent spectroscopy (FTPS) is performed on complete planar heterojunction solar cells and FIG. 5 shows the semi-log plot of external quantum efficiency (EQE) absorption edge of a device fabricated with the optimized precursor solution and annealing procedure. From this measurement, an Urbach energy ($E_u$) of 16.5 meV may be calculated very close to the values reported for the neat iodide perovskites. This shows that the crystalline compound of the invention has very favourable electron disorder.

Figure 6:
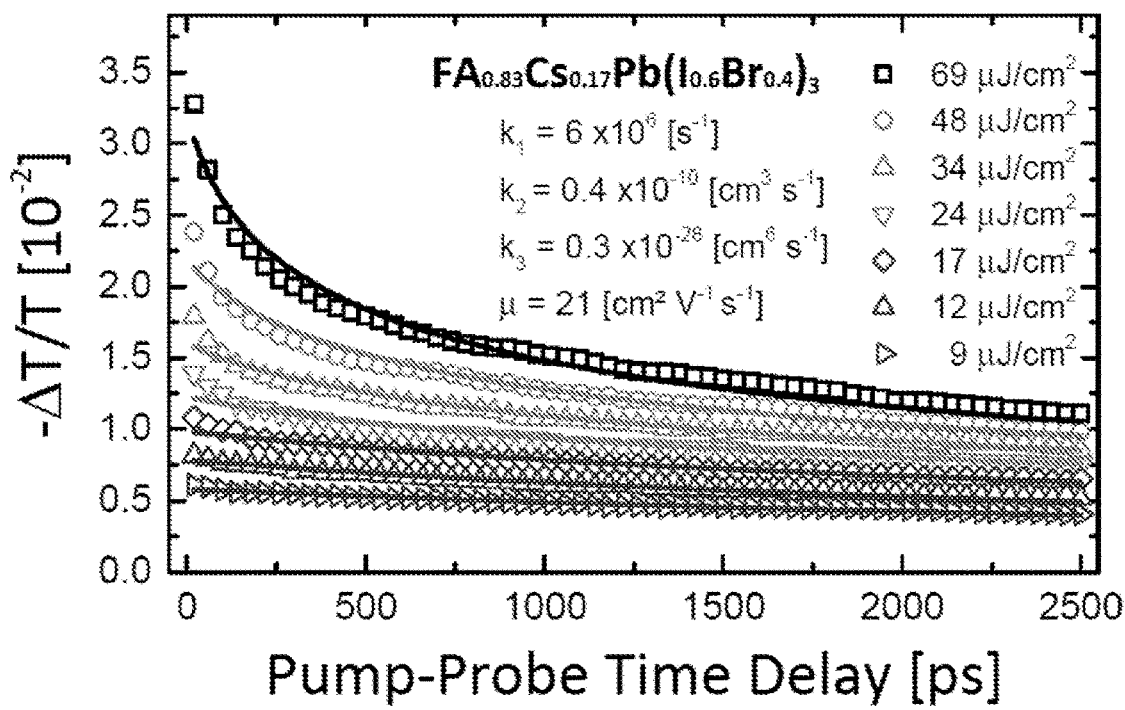
FIG. 6 shows OPTP transients for a $FA_{0.83}Cs_{0.17}Pb(I_{0.6}Br_{0.4})_3$ thin film, measured following excitation with a 35 fs light pulse of wavelength 400 nm with different fluences.

In order to further asses the electronic quantity of $FA_{0.83}Cs_{0.17}Pb(I_{0.6}Br_{0.4})_3$ the inventors have performed optical pump THz-probe (OPTP) spectroscopy, which is a non-contact method of probing the photoinduced conductivity and effective charge carrier mobility in the material. FIG. 6 shows the fluence-dependence of the OPTP transients, which exhibit accelerated decay dynamics at higher initial photoinjected charge-carrier densities, as the result of enhanced contributions from bimolecular and Auger recombination effects. The rate constants associated with different recombination mechanisms may be extracted by global fits to these transient of the solutions to the rate equation:

$$\frac{dn(t)}{dt} = -k_3 n^3 - k_2 n^2 - k_1 n$$

Figure 24:
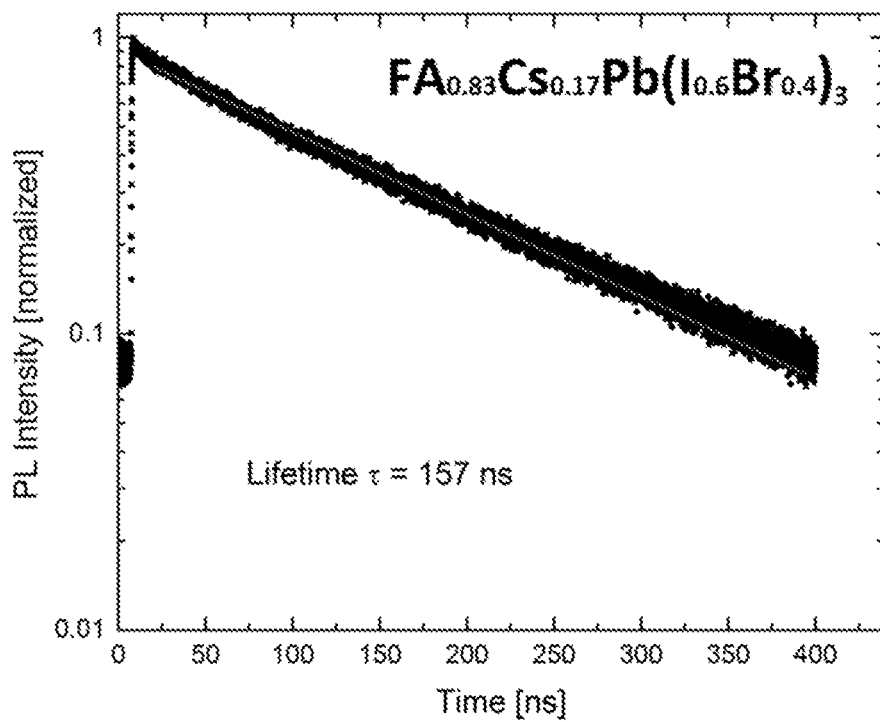
FIG. 24 shows time-resolved PL spectroscopy of $FA_{0.83}Cs_{0.17}Pb(I_{0.6}Br_{0.4})_3$ following excitation at 400 nm with an excitation fluence of 0.49 μJ cm$^{-2}$, measured under vacuum.

Here, $k_1$ is the monomolecular recombination rate associated with trap-related recombination, $k_2$ is the bi-molecular, and $k_3$ the Auger recombination rate constant. Since the monomolecular lifetime $\tau = k_1^{-1}$ is significantly longer (156 ns) than the 2.5 ns observation window of the OPTP measurements, $k_1$ is determined from monoexponential fits to the tail of the photoluminescence decay transient, as shown in FIG. 24. In addition, one is able to determine a value for the effective charge-carrier mobility from the initial value of the OPTP signal under knowledge of the absorbed photon density profile. In the absence of excitonic effects, this value approaches the sum of charge-carrier mobilities p for electrons and holes.

Figure 7:
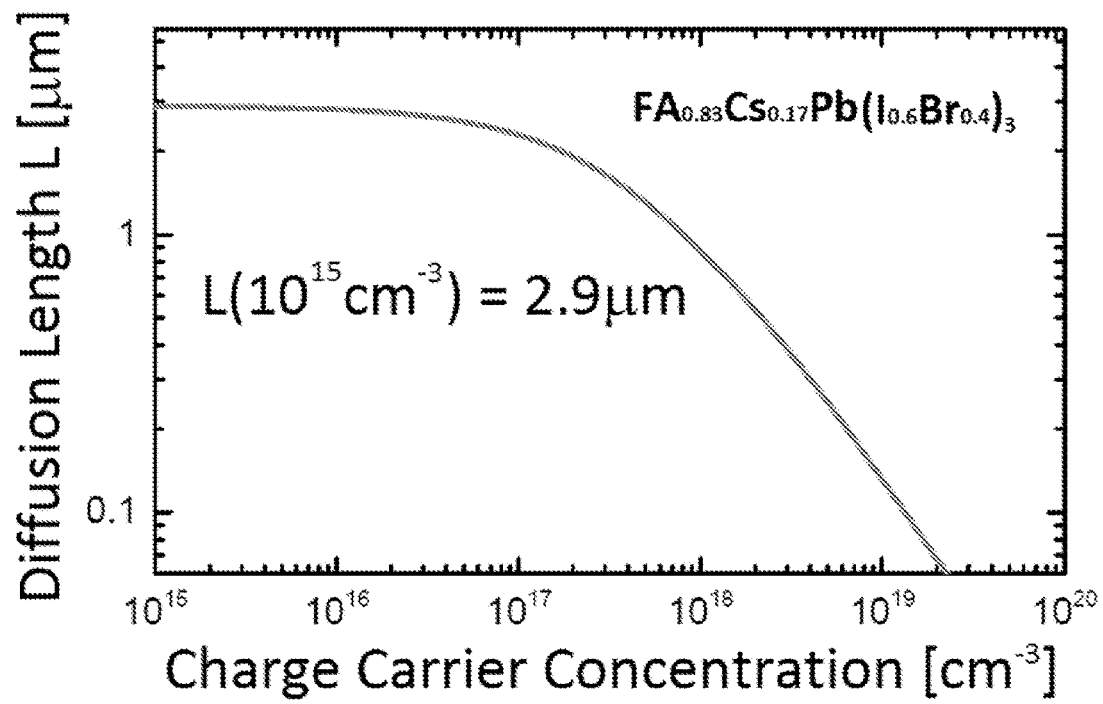
FIG. 7 shows charge-carrier diffusion length L as a function of charge concentration for the perovskite.

It has been found that $FA_{0.83}Cs_{0.17}Pb(I_{0.6}Br_{0.4})_3$ exhibits an excellent charge-carrier mobility of 21 cm$^2$/(Vs) which comes close to the value of ~30 cm$^2$/(Vs) typically found for high-quality single-halide $FAPbI_3$ and $MAPbI_3$ thin films at room temperature. This value is striking, because it has recently been shown that the corresponding neat-FA perovskite $FAPb(I_{0.6}Br_{0.4})_3$ only sustains very low charge-carrier mobilities <1 cm$^2$/(Vs) that are related to the amorphous and energetically disordered nature of these materials within the region of the trigonal to cubic phase transition. Conversely, $FA_{0.83}Cs_{0.17}Pb(I_{0.6}Br_{0.4})_3$ examined here displays a mobility value intermediate to those we have previously determined for $FAPbI_3$ (27 cm$^2$ V$^{-1}$ s$^{-1}$) and $FAPbBr_3$ (14 cm$^2$ V$^{-1}$ s$^{-1}$) suggesting that it is no longer limited by structural disorder. The inventors further assessed the potential of $FA_{0.83}Cs_{0.17}Pb(I_{0.6}Br_{0.4})$; for incorporation into planar heterojunction PV architectures by deriving the charge-carrier diffusion length $L=(\mu kT/(eR))^{0.5}$ as function of the charge-carrier density n, where $R=k_1+nk_2+n^2k_3$ is the total recombination rate, k the Boltzmann constant, T temperature and e the elementary charge. FIG. 7 shows that for charge-carrier densities typical under solar illumination (n~10$^{15}$ cm$^{-3}$) a value of L~2.9 μm is reached, which is comparable to values reported for high-quality thin films of neat lead iodide perovskites. The high charge-carrier mobility and slow recombination kinetics, and long charge carrier diffusion length imply that this mixed cation, mixed halide perovskite should be just as effective as a high quality solar cell absorber material as the neat halide perovskite $FAPbI_3$.

Figure 8:
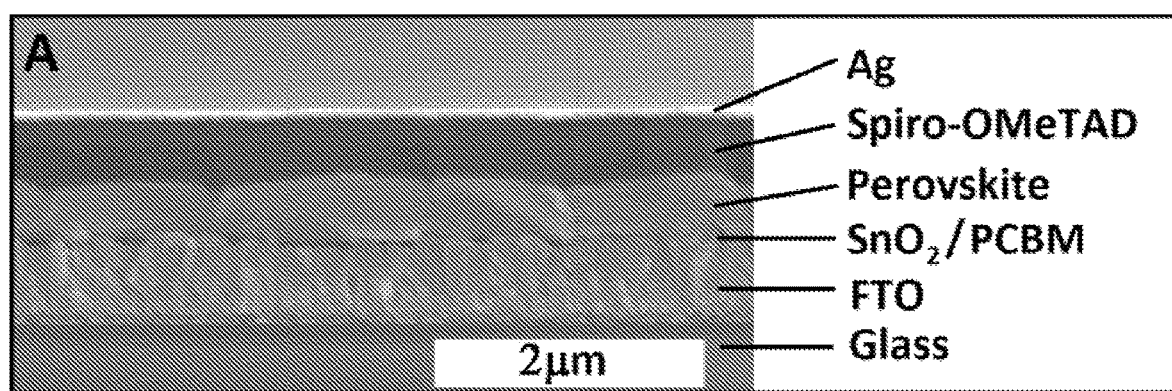
FIG. 8 shows a SEM image of cross-section of a planar heterojunction solar cell according to the invention.
Figure 9:
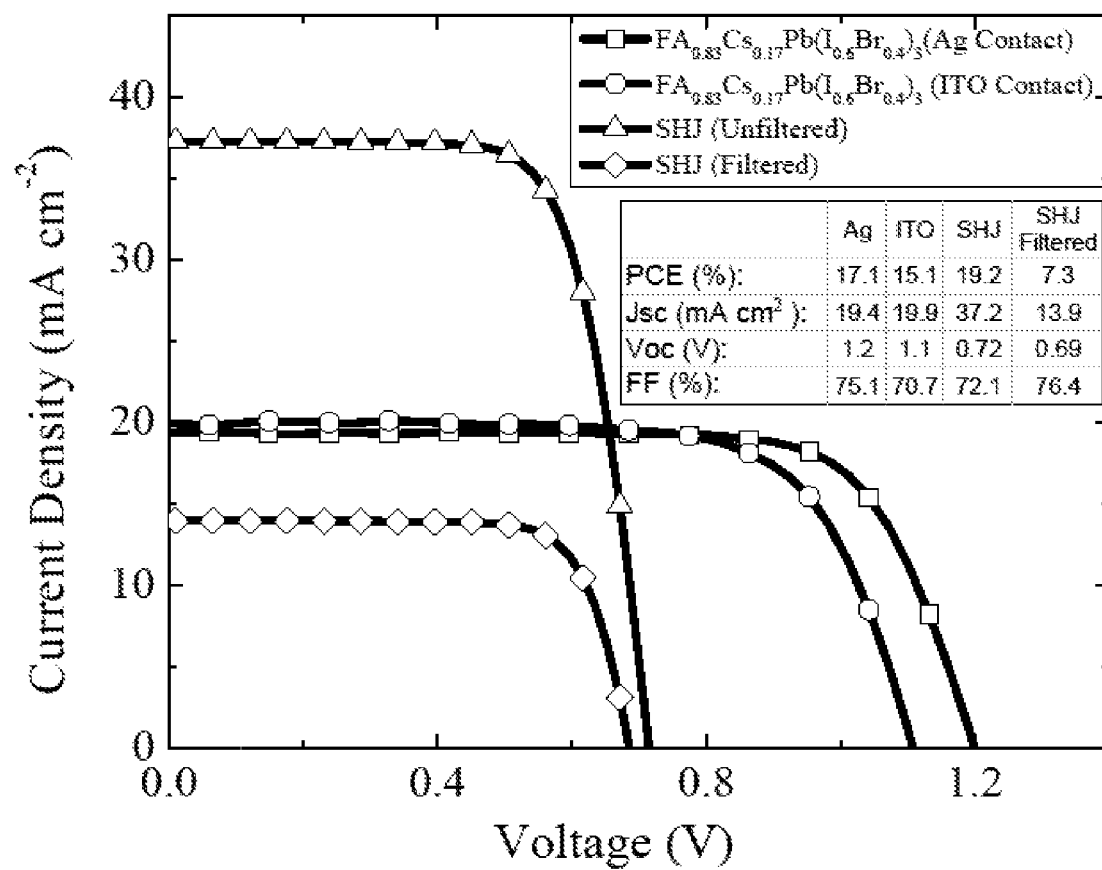
FIG. 9 shows forward bias to short-circuit J-V curve for the best perovskite devices fabricated, using a $SnO_2$/PCBM compact layer as the hole-blocking layer and Spiro-OMeTAD, as the electron-blocking hole collection layer with either a Ag metal, or semi-transparent ITO top electrode, measured at 0.38V/s scan rate.
Figure 10:
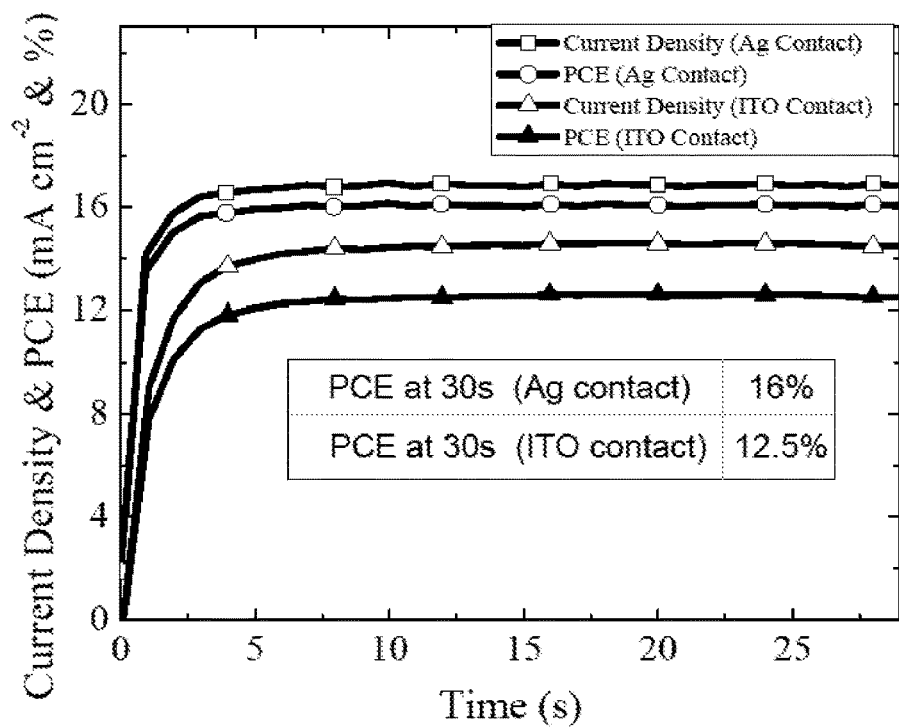
FIG. 10 shows photocurrent density and power conversion efficiency measured at maximum power point for a 30 s timespan.
Figure 11:
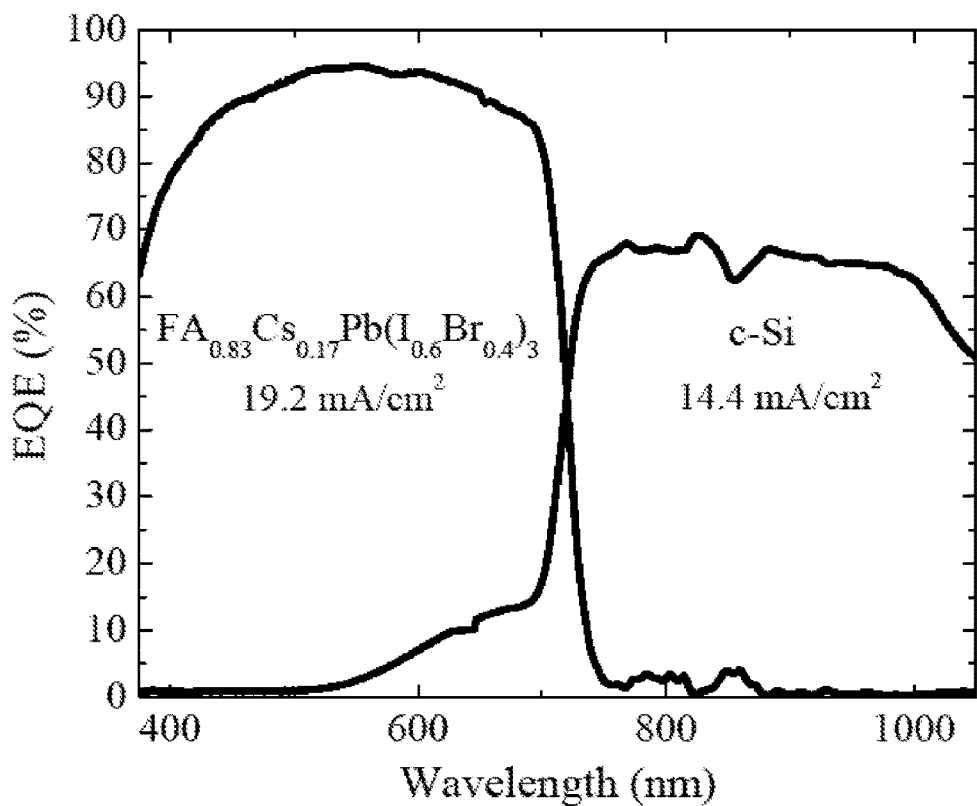
FIG. 11 shows external quantum efficiency (EQE) spectrum measured in short-circuit ($J_{SC}$) configuration for the highest efficiency perovskite cell and the SHJ cell measured with the simulated sun light filtered through the semi-transparent perovskite cell.
Figure 25:
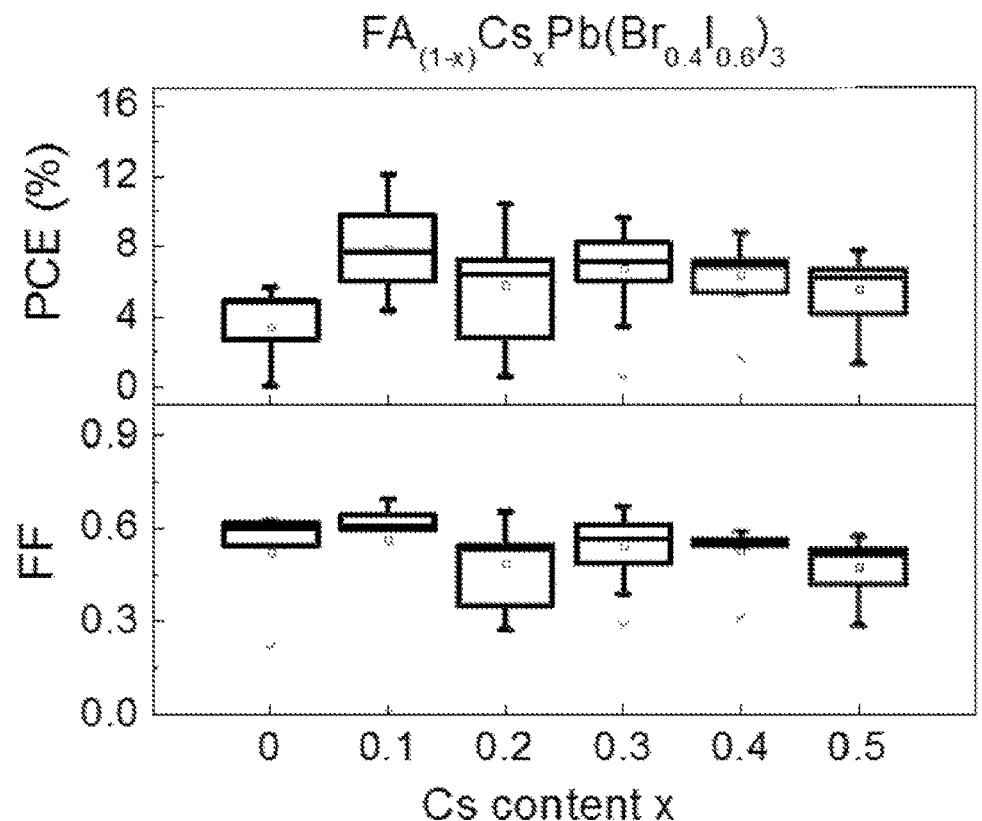
FIG. 25 shows (top) Power conversion efficiency (PCE) of composition ranging from x=0 to 0.5 of Cs and (bottom) Fill Factor (FF) of composition ranging from x=0 to 0.5 of Cs.
Figure 26:
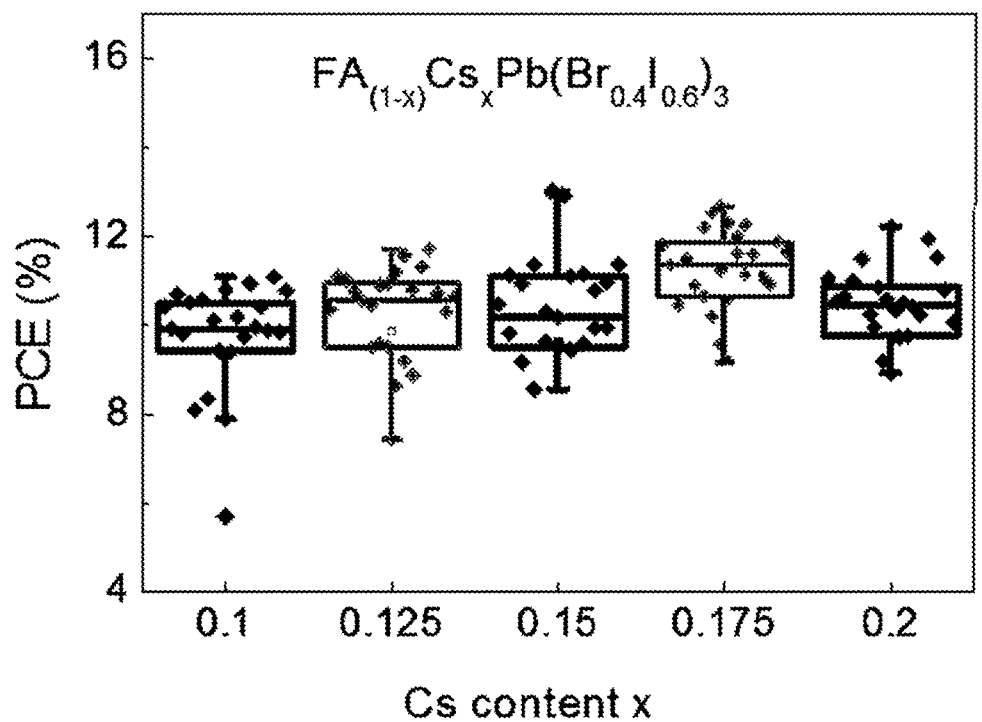
FIG. 26 shows the PCE of devices containing perovskites having a composition ranging from x=0 to 0.2 of Cs.
Figure 27:
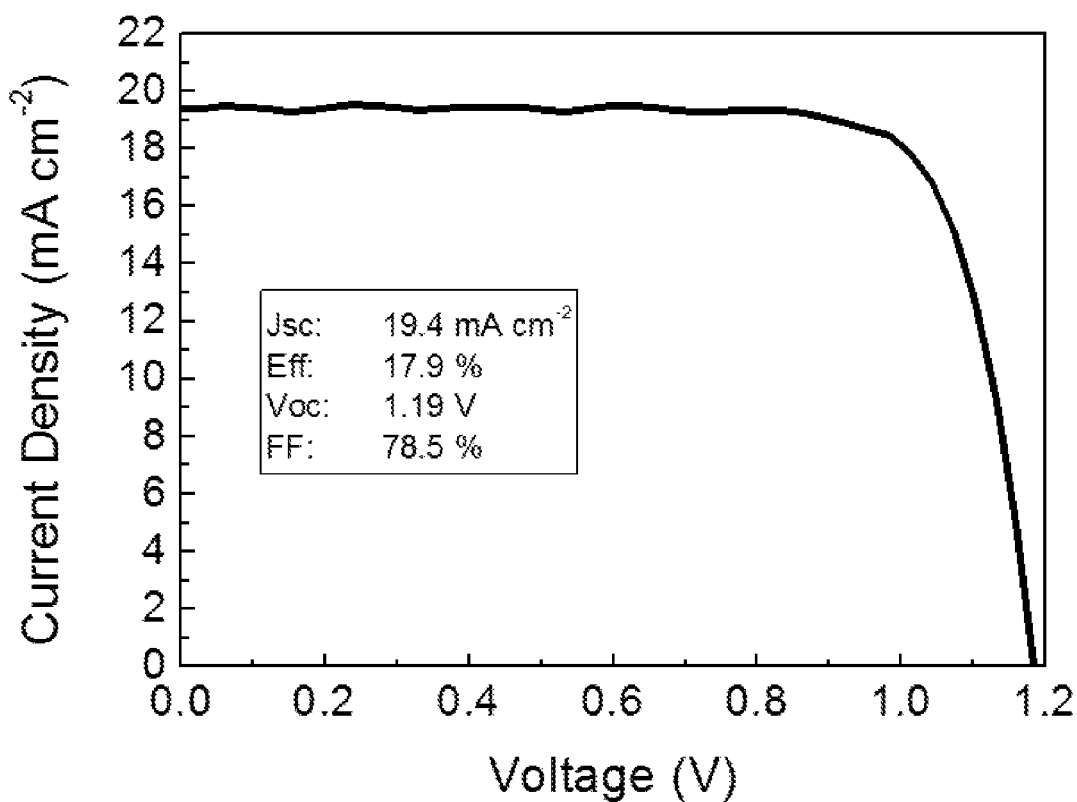
FIG. 27 shows J-V characteristics of a device having a FTO/SnO$_2$/PCBM/perovskite/Spiro-OMeTAD/Ag architecture under simulated air-mass (AM) 1.5 100 mW cm$^{-2}$ sun light using a 0.38V/s scan rate and photocurrent density and power conversion efficiency as a function of time held at maximum power voltage. The perovskite was obtained from the optimized precursor solution composition of $FA_{0.83}Cs_{0.17}Pb(I_{0.6}Br_{0.4})_3$.
Figure 28:
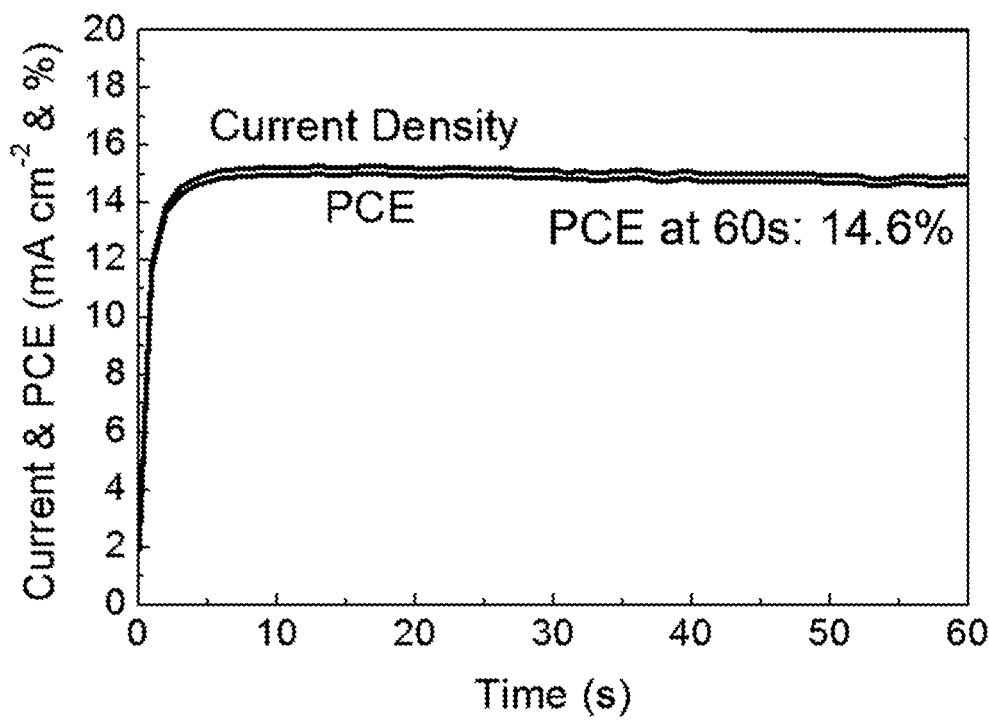
FIG. 28 shows photocurrent density and power conversion efficiency measured over 1 minute for the device of FIG. 27.
Figure 29:
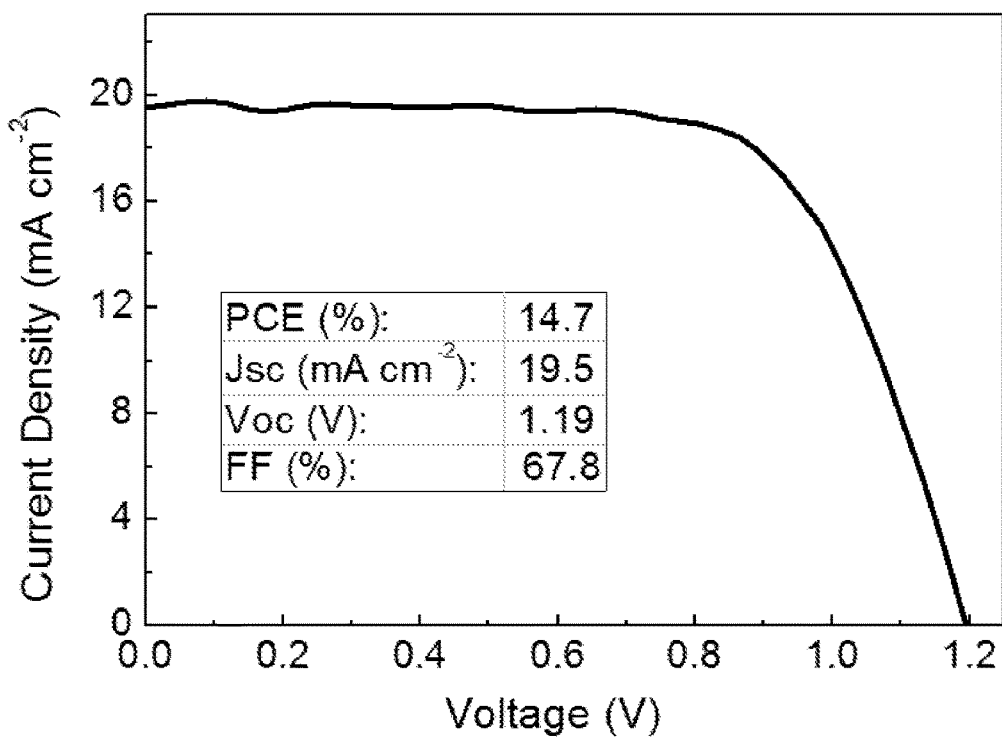
FIG. 29 shows J-V characteristics of FTO/SnO$_2$/PCBM/perovskite/Spiro-OMeTAD/Ag architecture measured using an active area and masked aperture of 0.715 cm$^2$, under simulated air-mass (AM) 1.5, 109 mW cm$^{-2}$ sun light using a 0.38V/s scan rate and photocurrent density and power conversion efficiency as a function of time held at maximum power voltage obtained for the optimized precursor solution composition of $FA_{0.83}Cs_{0.17}Pb(I_{0.6}Br_{0.4})_3$.
Figure 30:
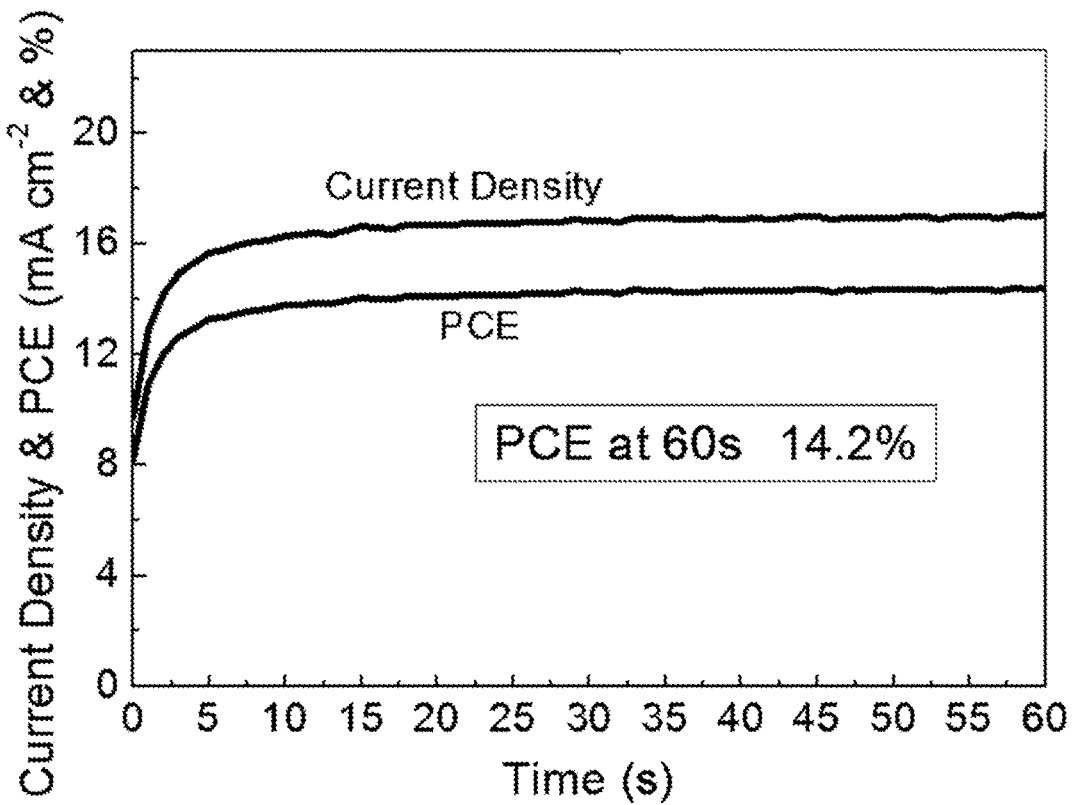
FIG. 30 shows photocurrent density and power conversion efficiency measured over 1 minute for the device of FIG. 29.

A series of planar heterojunction solar cells were fabricated to assess the overall solar cell performance. Data for solar cells fabricated with a range of compositional and processing parameters are shown in FIGS. 25 and 26. The device architecture is shown in FIG. 8, which is composed of a $SnO_2$/Phenyl-C60-butyric acid methyl ester ($PC_{60}BM$) electron selective layer, a solid $FA_{0.83}Cs_{0.17}Pb(I_{0.6}Br_{0.4})_3$ perovskite absorber layer, and Li-TFSI-doped Spiro-OMeTAD with 4-tert-Butylpyridine (TBP) additive as the hole-collection layer, caped with an Ag electrode. Current-voltage characteristics of such devices under simulated air-mass (AM) 1.5 100 mW $cm^{-2}$ sun light were measured, and the current-voltage characteristics of one the highest performing device is shown in FIG. 9. The device delivers a short-circuit current density of 19.4 mA $cm^{-2}$, an open-circuit voltage of 1.2 V, and a PCE of 17.1%. By holding the cell at a fixed maximum power point forward bias voltage of 0.95V the power output over time was measured as reaching a stabilized efficiency of 16%, which is shown in FIG. 10. The highest JV efficiency we measured was 17.9%, which is shown in FIGS. 27 and 28. To demonstrate that these cells can also operate with larger area, 0.715 $cm^2$ active layers were fabricated where the cells reach a stabilized power output of over 14%, as shown in FIGS. 29 and 30. FIG. 11 shows the spectral response of the solar cell, which confirms the wider band gap of the solar cell, and also integrates over the AM 1.5 solar spectrum to give 19.2 $mAcm^{-2}$, in close agreement to the measured $J_{SC}$ of the solar cell.

Figure 31:
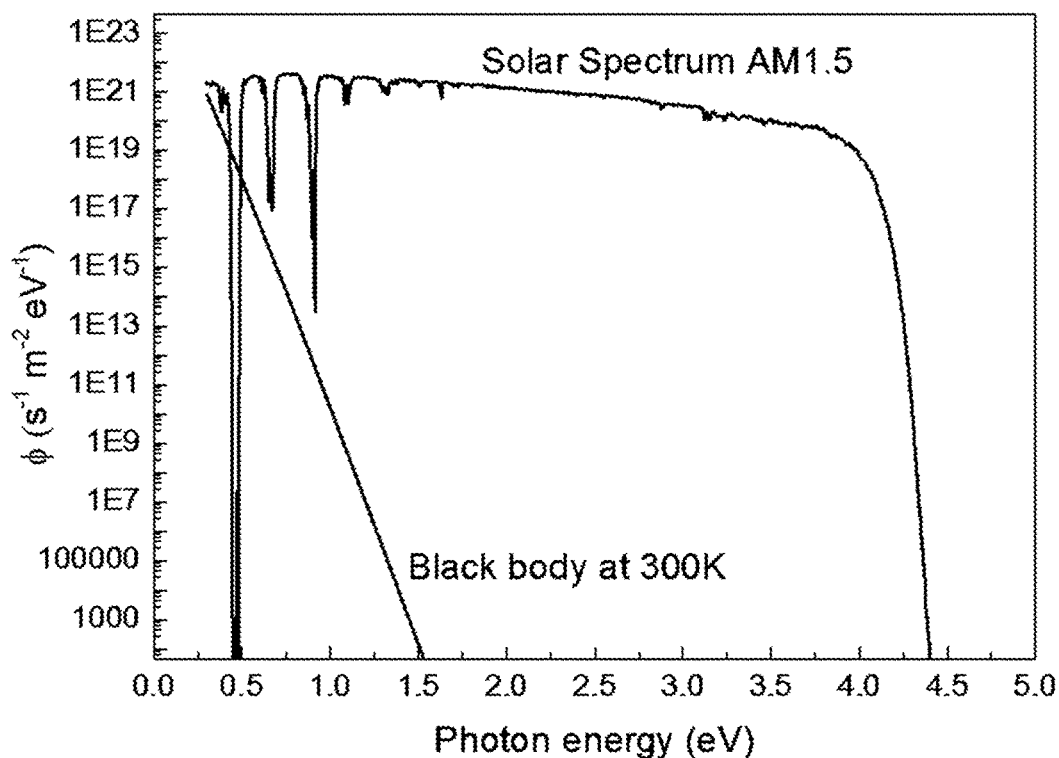
FIG. 31 shows the calculated photon flux of black body at 300K compared to AM 1.5 solar spectrum photon flux.

This performance is very competitive with the best reported single junction perovskite solar cell reported so far, especially considering the wider band gap of compound of the invention which should result in a few % absolute efficiency drop with respect to a 1.55 eV material. Importantly for tandem solar cells, the 1.74 eV material appears to be capable of generating a higher open-circuit voltage than the 1.55 eV tri-iodide perovskites in planar heterojunction solar cells. The maximum attainable $V_{OC}$ for a solar cell absorber material is shown in FIG. 31. For the $FA_{0.83}Cs_{0.17}Pb(I_{0.6}Br_{0.4})_3$ device, a maximum $V_{OC}$ of 1.42 V is estimated which is 100 mV higher than that estimated for $MAPbI_3$ devices. The crystalline material of the invention will thus deliver a higher voltage. It is also notable that with 1.2V $V_{OC}$, a loss of around 220 mV is still present as compared to the predicted $V_{OC}$ in the radiative limit, indicating much scope for further improvement by better selection and optimization of contact materials and inhibition of non-radiative decay channels from within the perovskite.

Figure 32:
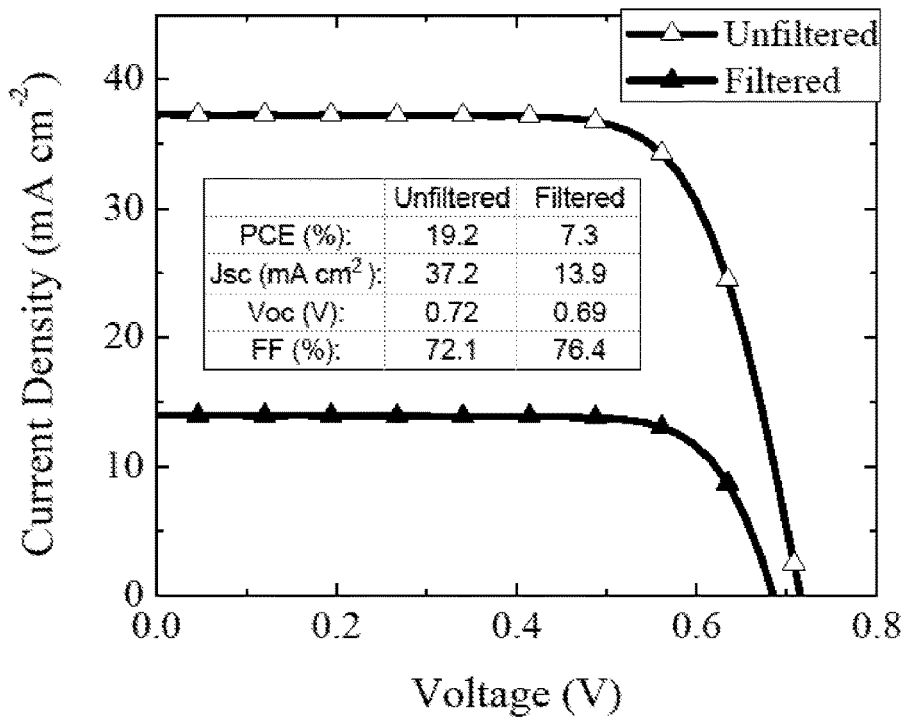
FIG. 32 shows current-voltage characteristics of unfiltered and filtered SHJ cell under simulated air-mass (AM) 1.5 100 mW cm$^{-2}$ sun light. The SHJ cell was filtered using a $FA_{0.83}Cs_{0.17}Pb(I_{0.6}Br_{0.4})_3$ with semi-transparent ITO rear-contact.

In order to demonstrate the potential impact of employing this new perovskite composition in a tandem architecture, semitransparent perovskite solar cells were fabricated by sputter coating ITO on top of the perovskite cells, with the additional inclusion of a thin "buffer layer" of solution processed ITO nanoparticles between the spiro-OMeTAD and the ITO in order to inhibit sputter damage to the perovskite cell. The efficiency of the semi-transparent $FA_{0.83}Cs_{0.17}Pb(I_{0.6}Br_{0.4})_3$ solar cells was 15.1%, as determined by the current voltage curve, with a stabilized power output of 12.5%. Since the $J_{SC}$ is very similar to the cell with the Ag electrode, it is expected that the slight drop in $V_{OC}$ and SPO will be surmountable by better optimization of the ITO sputter deposition procedure. A silicon heterojunction (SHJ) cell was measured with and without a semi-transparent perovskite cell held in front of it, and an efficiency of 7.3% filtered was determined and 19.2% when uncovered, as shown in FIG. 32. These results demonstrate the feasibility of obtaining a combined tandem solar cell efficiency ranging from 19.8% (if the) are combined with the stabilized power output of the semi-transparent cell) to 25.2% (if they are combined with the highest JV measured efficiency of the $FA_{0.83}Cs_{0.17}Pb(I_{0.6}Br_{0.4})_3$ cell).

In summary, the inventors have tailored a perovskite composition to be perfectly suited for incorporation into silicon tandem solar cells. They have addressed the critical issues that were limiting the use of perovskite as a viable top-cell material for tandem applications, and delivered a thermally, structurally and compositionally stable material of the correct band gap. Surprisingly, these $FA_{0.83}Cs_{0.17}Pb(I_{0.6}Br_{0.4})_3$ films exhibit a very steep rise in absorption and EQE onset below the band gap, an excellent charge-carrier mobility of 21 $cm^2/(Vs)$ and diffusion length of ~3 µm, all of which indicate that is electronically homogeneous with low energetic disorder and as high a quality semiconductor as the tri-iodide perovskites. Moreover, the inventors have fabricated solar cells reaching high voltages in excess of 1.2V and achieving over 17% power conversion efficiency and an SPO of 16% in single junctions. They have additionally demonstrated the feasibility of creating perovskite silicon tandem solar cells with efficiencies ranging from 19.8 to 25.2%. Considering further minor improvements in the perovskite, optical management and integration and choice of silicon rear cell, it is feasible that this system could deliver up to 30% efficiency in the near future. In addition, this monotonic tunability of band gap across the visible spectrum within a single crystalline phase, will have direct impact to the color tunability and optimization of perovskites for light emitting applications.

Example 2—Variation of Br Content

Figure 33:
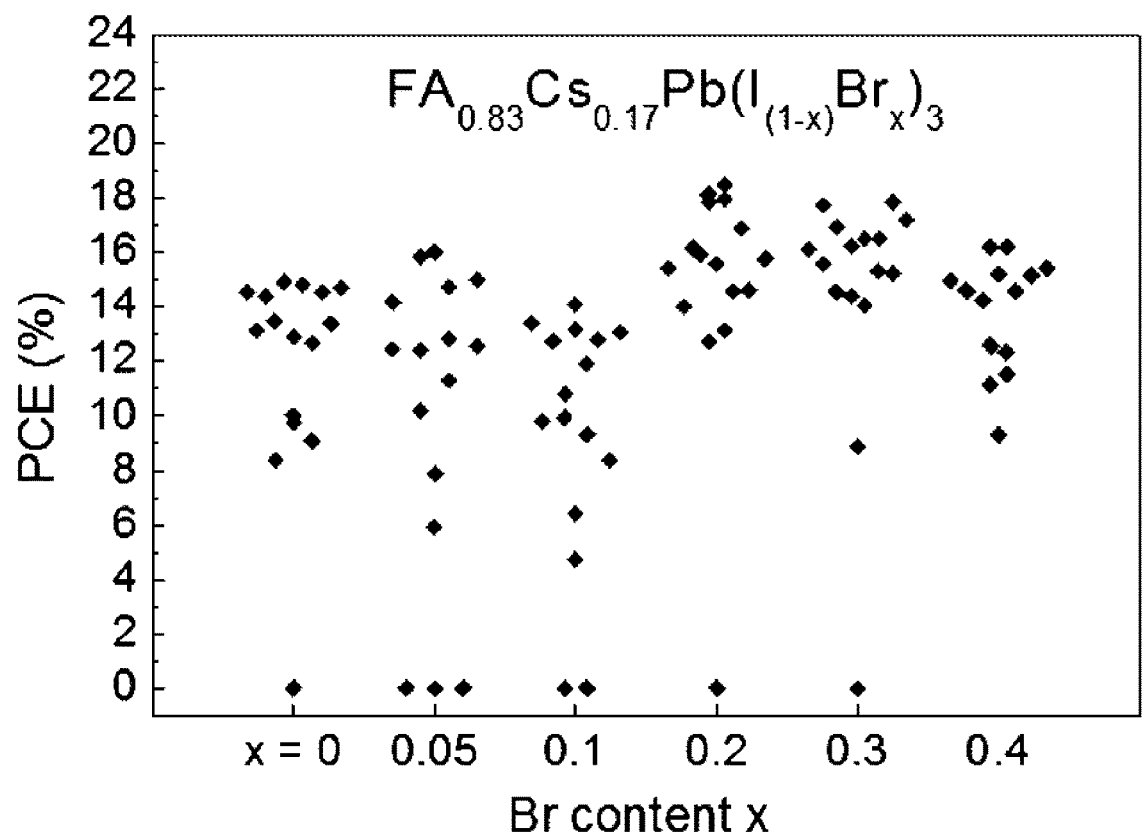
FIG. 33 shows device performance of a series of $FA_{0.83}Cs_{0.17}Pb(I_{(1-x)}Br_x)_3$ with various I/Br compositions, and in particular power conversion efficiency (PCE) of composition ranging from x=0 to 0.4 of Br.

Devices containing various perovskites of the formula $FA_{0.83}Cs_{0.17}Pb(I_{(1-x)}Br_x)_3$ were synthesis by a method equivalent to that described in Example 1. The PCE of each device was evaluated as for Example 1 and the results are shown in FIG. 33. The devices generally perform well with different bromine contents, and an improvement is observed for contents of over 10%.

Example 3—Electroluminescence Studies

Examples 1 and 2 concern the photoabsorbent properties of the mixed cation/mixed halide perovskites of the invention. The crystalline compounds of the invention have also been found to be effective photoemissive compounds. As such, light emitting devices could be constructed containing the crystalline compounds of the invention.

In particular, a series of $FA_{0.825}Cs_{0.175}Pb(I_{(1-x)}Br_x)_3$ with x=[0, 0.05, 0.1, 0.2, 0.3, 0.4] devices was prepared following the same fabrication method described for photovoltaic devices. To measure the electroluminescence intensity, the devices were kept in a chamber filled with Nitrogen and placed inside an integrating sphere. The emitted light is collected with a fiber and analysed with a fixed grating CCD spectrometer (Maya Pro, Ocean Optics). The intensity of the luminescence is estimated from the area of the luminescence peak. The current-voltage (IV) properties are measured simultaneously with a Keithley sourcemeter (Model 2600).

Figure 34:
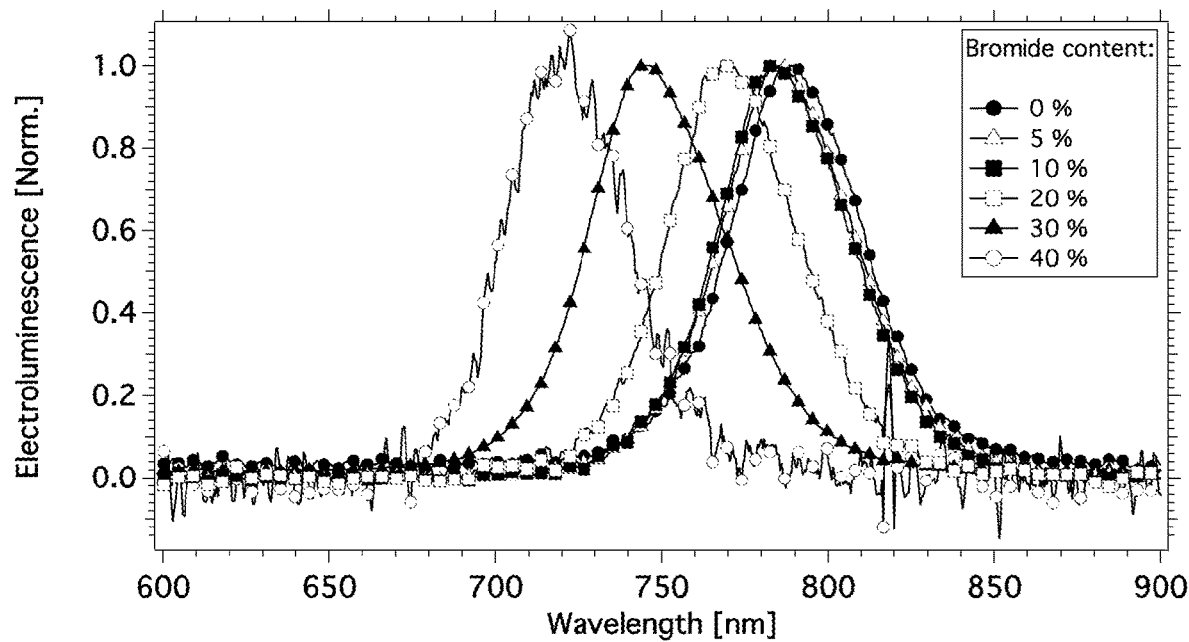
FIG. 34 shows the normalized electroluminescence spectra of the series of $FA_{0.825}Cs_{0.175}Pb(I_{(1-x)}Br_x)_3$ devices with x=[0, 0.05, 0.1, 0.2, 0.3, 0.4].
Figure 35:
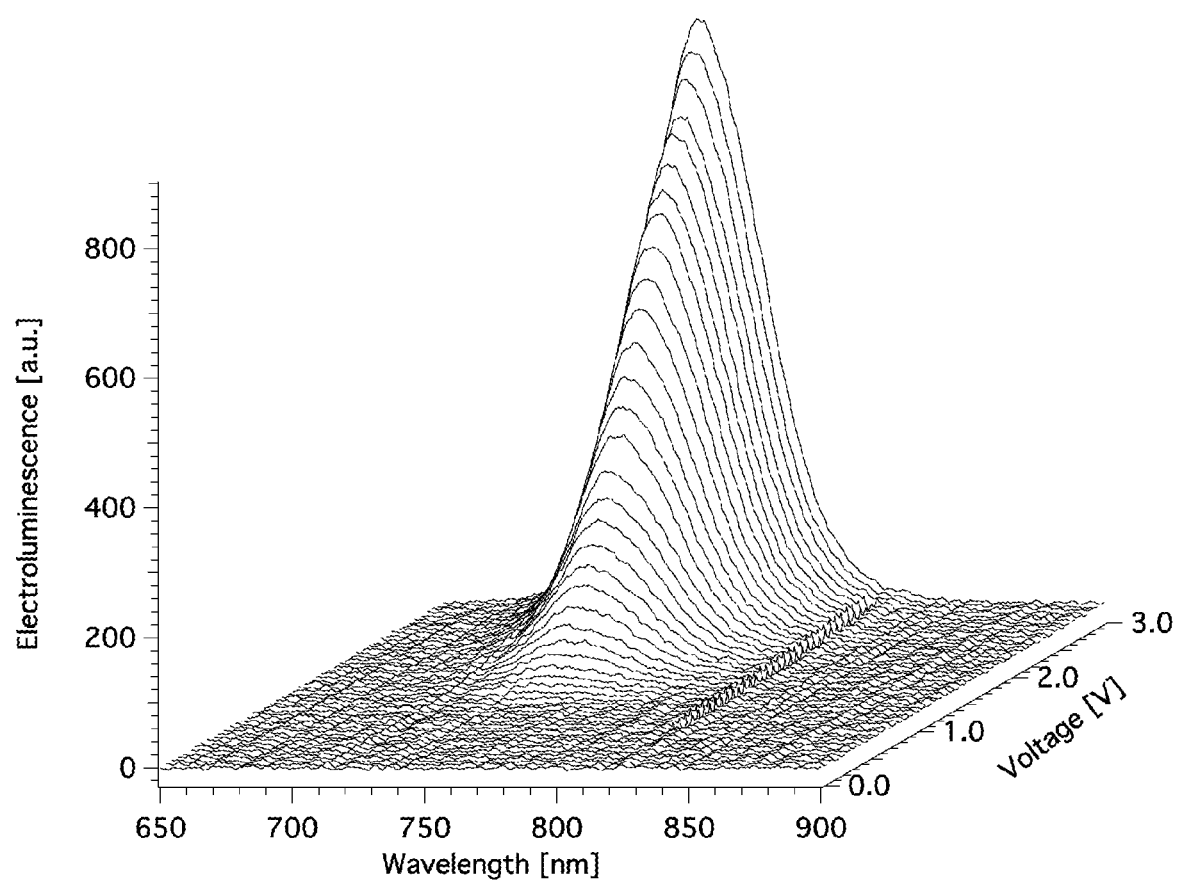
FIG. 35 shows the electroluminescence spectra of $FA_{0.825}Cs_{0.175}Pb(I_{(1-x)}Br_x)_3$ with x=0.3 as a function of applied voltage.
Figure 36:
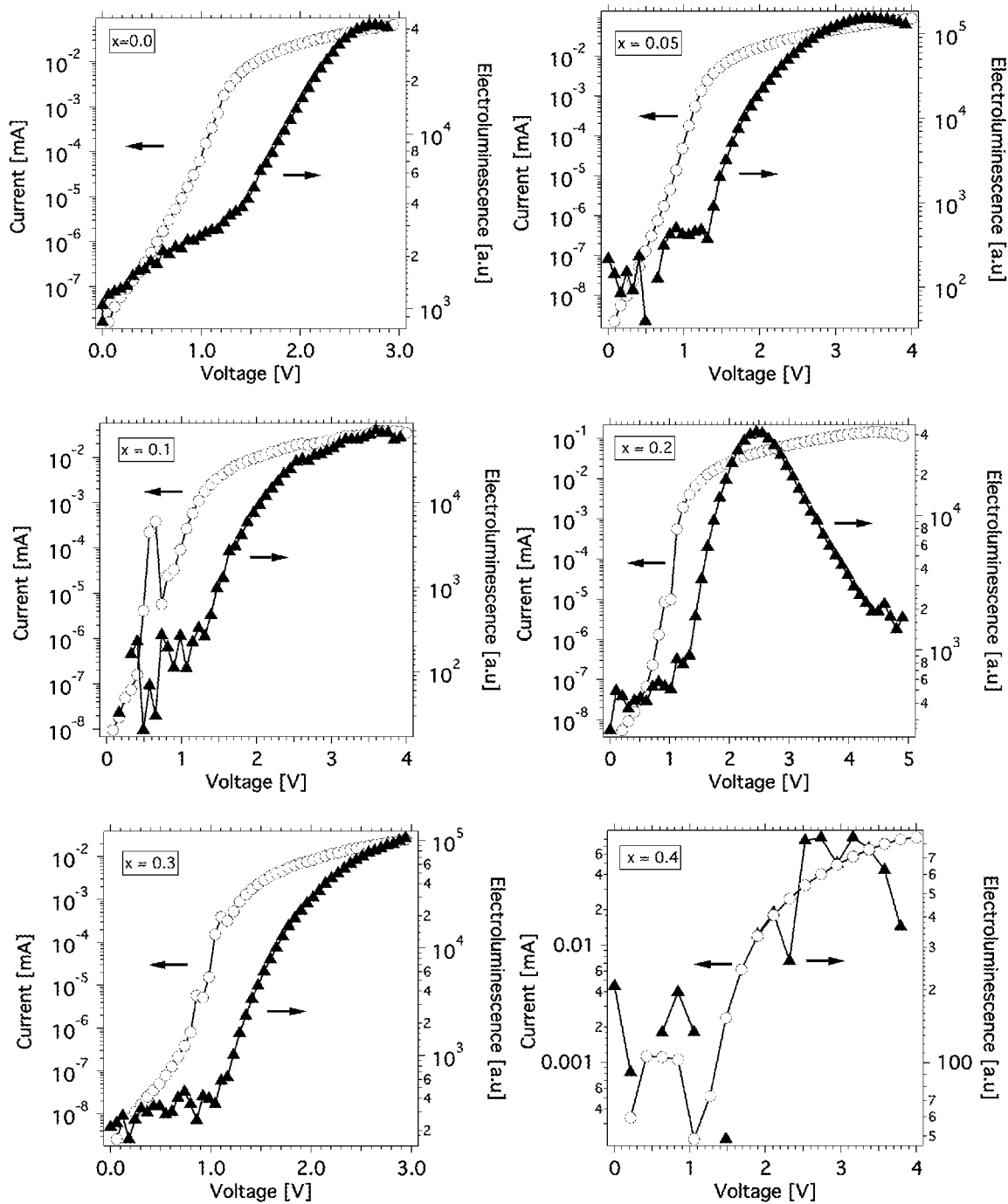
FIG. 36 shows IV and LV performance for the series of $FA_{0.825}Cs_{0.175}Pb(I_{(1-x)}Br_x)_3$ with x=[0, 0.05, 0.1, 0.2, 0.3, 0.4]. The cell area was 0.909 cm$^2$.

FIG. 34 shows the normalized electroluminescence spectra of the series of $FA_{0.825}Cs_{0.175}Pb(I_{(1-x)}Br_x)_3$ devices with x=[0, 0.05, 0.1, 0.2, 0.3, 0.4]. FIG. 35 shows the electroluminescence spectra of $FA_{0.825}Cs_{0.175}Pb(I_{(1-x)}Br_x)_3$ with x=0.3 as a function of applied voltage. The plots in FIG. 36 show IV and LV performance for the series of $FA_{0.825}Cs_{0.175}Pb(I_{(1-x)}Br_x)_3$ with x=[0, 0.05, 0.1, 0.2, 0.3, 0.4]. The cell area was 0.909 cm².

Example 4—Comparative Stability Study

In order to assess the long term operational stability of $FA_{0.83}Cs_{0.17}Pb(I_{0.6}Br_{0.4})_3$ solar cells, stability measurements were performed for solar cells comprising the mixed-cation lead mixed-halide perovskite as the absorber layer. The stability of solar cells comprising the mixed-cation perovskite according to the invention were compared with reference devices comprising the methylammonium lead halide perovskite $MAPbI_xCl_{3-x}$ as the absorber.

The devices comprised a layer of $C_{60}$ disposed on a $SnO_2$ electron transport layer. The $C_{60}$ layer was doped or undoped with N-DPBI (dihydro-1H-benzoimidazol-2-yl). The device configuration was $FTO/SnO_2/C_{60}$ (neat or 1 wt % doped)/perovskite/spiro-OMeTAD(doped with Li-TFSI and tBP)/Au. The devices were aged under full spectrum simulated AM 1.5, 76 mWcm⁻² average irradiance at $V_{OC}$ in air without a UV filter.

Figure 37:
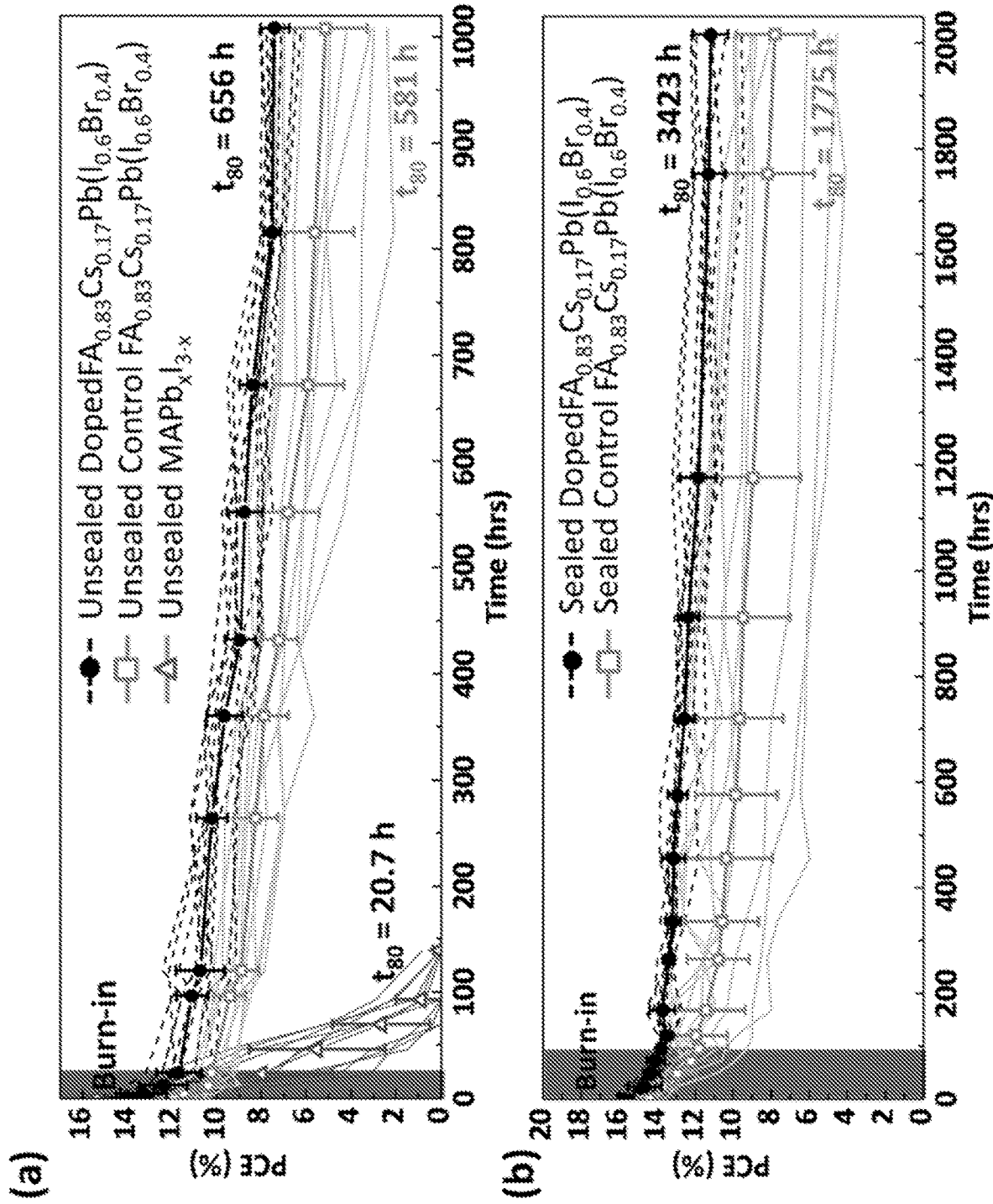
FIG. 37 shows the comparison of the stability of devices comprising the mixed-cation perovskite according to the invention and a methylammonium lead halide perovskite. In the figure legend, "doped" refers to a cell containing an n-doped C$_{60}$ n-type electron collection layer, "control" refers to a cell containing a neat C$_{60}$ n-type electron collection layer, without additional n-doping.

The results for the cells light soaked (AM 1.5 full spectrum light) at $V_{OC}$ in air with ambient humidity (~55%) are shown in FIG. 37. The cells in FIG. 37(a) are not encapsulated. The cells comprising this $FA_{0.83}Cs_{0.17}Pb(I_{0.6}Br_{0.4})_3$ perovskite exhibits a much stronger resistance to degradation under the aging conditions tested. All cells exhibit a fast degradation over the first 50 hrs, with the $MAPbI_xCl_{3-x}$ cell degrading to approximately zero % efficiency over this time. In contrast, the $FA_{0.83}Cs_{0.17}Pb(I_{0.6}Br_{0.4})_3$ cells only degrade by a few % absolute efficiency over this time, and then proceed to degrade at a much slower linear rate. The stability of devices comprising the mixed-cation perovskite according to the invention which have been encapsulated with a hot-melt polymer foil and glass cover-slip are shown in FIG. 37(b). These results show that the mixed-cation perovskite is much more stable in general than the $MAPbI_xCl_{3-x}$ perovskite. This is both thermal and moisture stability, and importantly stability to operation in the presence of oxygen.

Example 5—Absorbance, Luminescence and XRD Studies of Mixed-Cation Perovskites

Layers of $FA_{0.83}Cs_{0.17}Pb(Cl_xBr_yI_z)_3$ perovskites were formed on fluorine-doped tin oxide (FTO) coated glass substrates and annealed at 150° C. for 30 min in nitrogen, using a 0.1 M solution dissolved in a 4:1 DMF:DMSO solvent mixture and a nitrogen flow to quench crystallization during spin-coating.

Figure 38:
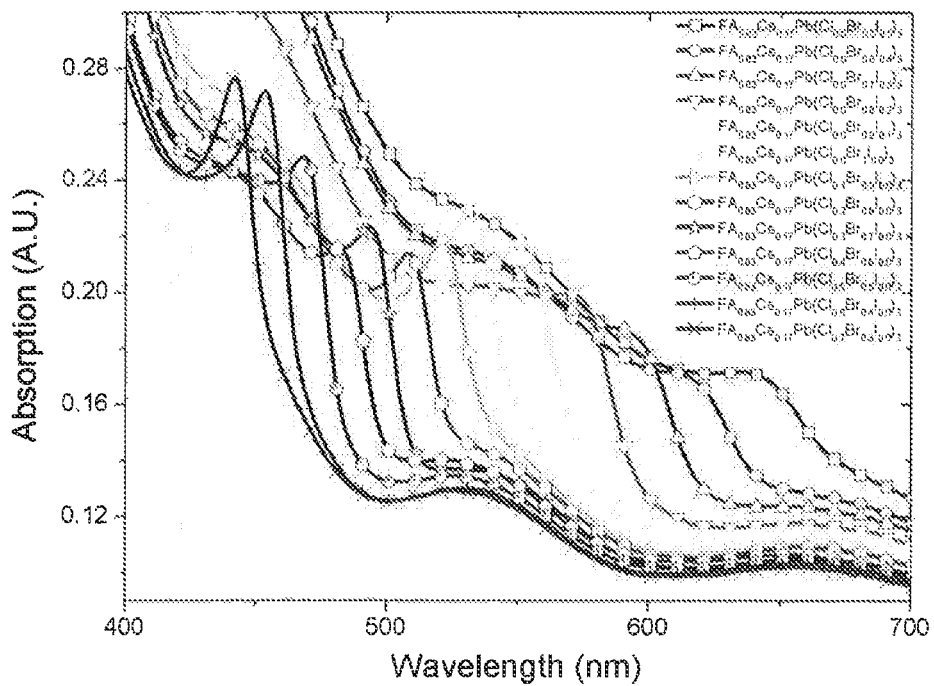
FIG. 38 shows the UV-Vis absorbance spectra for the visible range of $FA_{0.83}Cs_{0.17}Pb(Cl_xBr_yI_z)_3$ perovskites formed on fluorine-doped tin oxide (FTO) coated glass substrates.

The UV-vis absorbance spectra of the perovskites were measured and the results are shown in FIG. 38.

Figure 39:
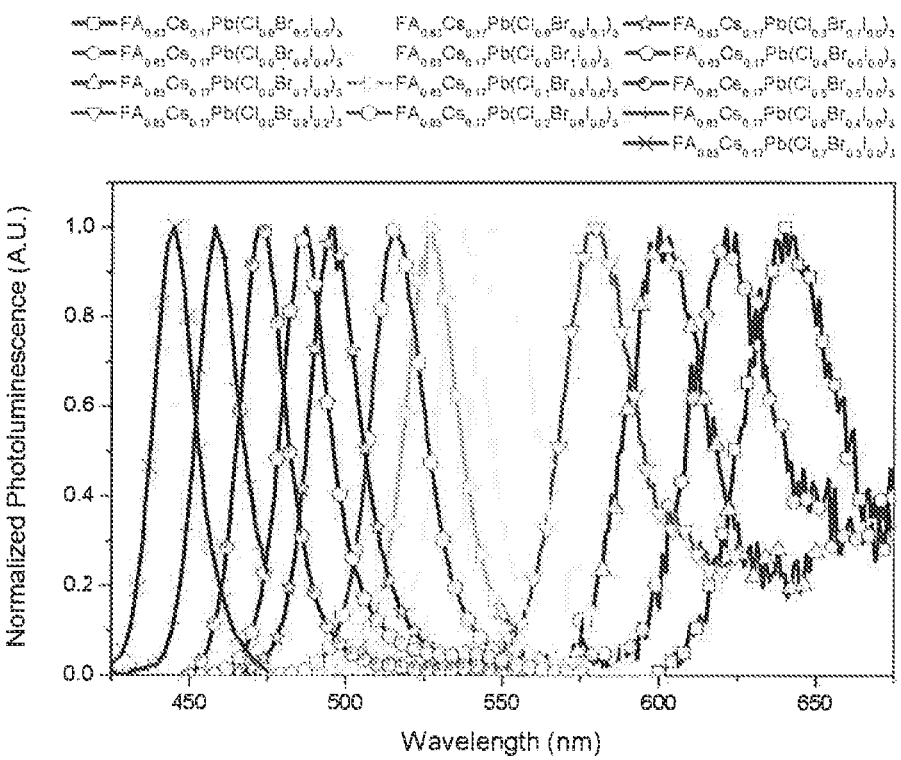
FIG. 39 shows the normalized photoluminescence spectra for the visible range of $FA_{0.83}Cs_{0.17}Pb(Cl_xBr_yI_z)_3$ perovskites formed on fluorine-doped tin oxide (FTO) coated glass substrates.

The normalized photoluminescence spectra for the visible range of the perovskites were measured and the results are shown in FIG. 39. Excitation wavelength varied from 375 nm to 600 nm.

Figure 40:
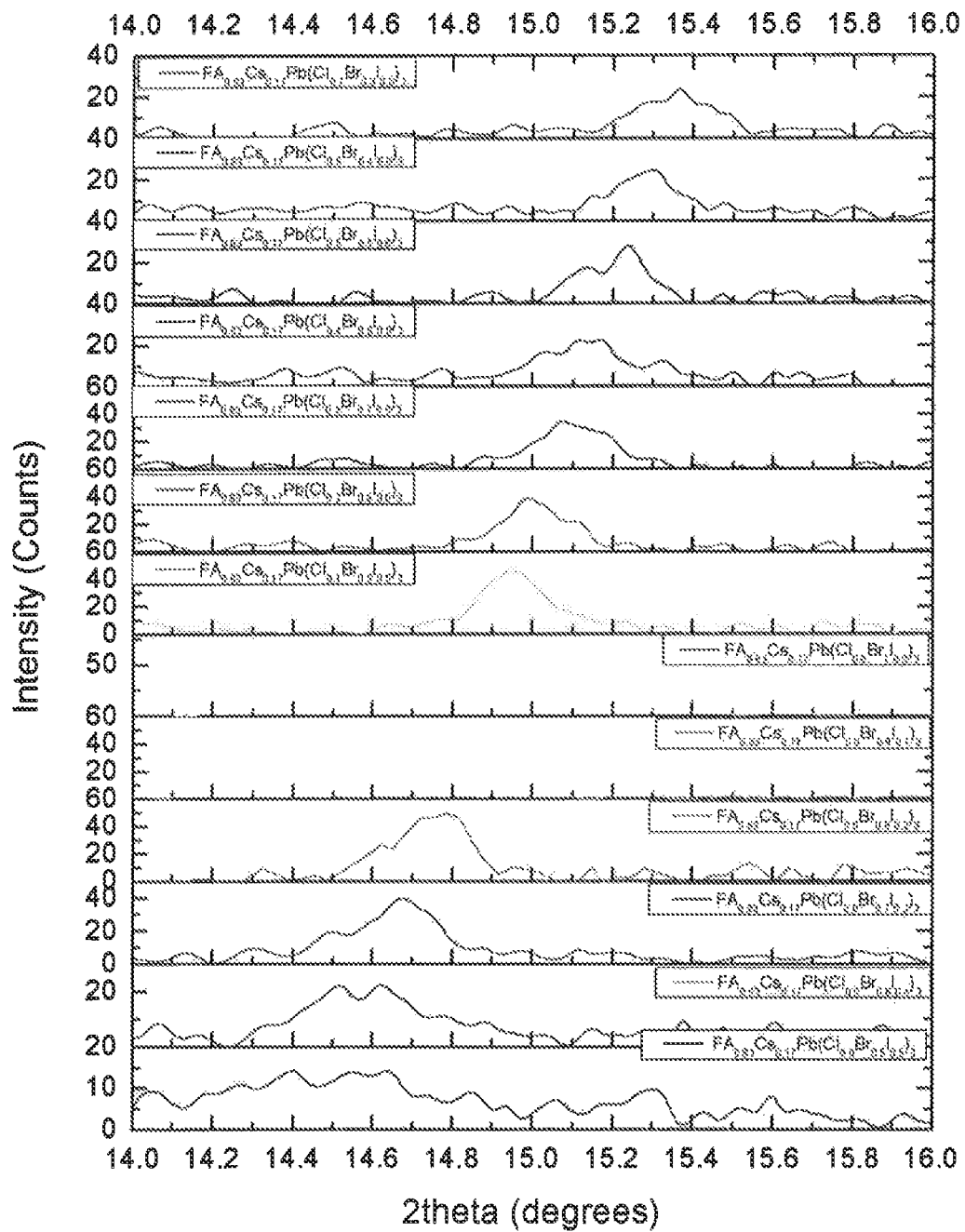
FIG. 40 shows the x-ray diffraction pattern (XRD) for the visible range of $FA_{0.83}Cs_{0.17}Pb(Cl_xBr_yI_z)$ perovskites formed on fluorine-doped tin oxide (FTO) coated glass substrates

X-ray diffraction patterns (XRD) of the perovskites were measured and the results are shown in FIG. 40.

The invention claimed is:

1. A crystalline compound which is a perovskite of formula:

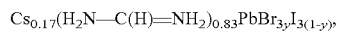

$Cs_{0.17}(H_2N-C(H)=NH_2)_{0.83}PbBr_{3y}I_{3(1-y)}$, wherein y is from 0.01 to 0.99.

2. A crystalline compound according to claim 1, wherein y is from 0.01 to 0.70 or
y is from 0.20 to 0.60.

3. A crystalline compound according to claim 1, wherein y is from 0.30 to 0.50.

4. A crystalline compound according to claim 1, wherein the crystalline compound is $Cs_{0.17}(H_2N-C(H)=NH_2)_{0.83}Pb(Br_{0.4}I_{0.6})_3$.

5. A crystalline compound according to claim 1, wherein the crystalline compound is $Cs_{0.175}(H_2N-C(H)=NH_2)_{0.825}Pb(Br_{0.4}I_{0.6})_3$.

6. A crystalline compound according to claim 1, wherein the crystalline compound has a band gap of from 1.5 to 2.0 eV.

7. A crystalline compound according to claim 1, wherein the crystalline compound is in the form of particles comprising the crystalline compound.

8. A semiconducting material comprising a crystalline compound which is a perovskite of formula $Cs_{0.17}N(H_2N-C(H)=NH_2)_{0.83}PbBr_{3y}I_{3(1-y)}$, wherein y is from 0.01 to 0.99.

9. A semiconducting material according to claim 8, wherein the semiconducting material comprises greater than or equal to 80% by weight of the crystalline compound.

10. A semiconductor device comprising a semiconducting material, which semiconducting material comprises a crystalline compound, which crystalline compound comprises a perovskite of formula $Cs_{0.17}(H_2N-C(H)=NH_2)_{0.83}PbBr_{3y}I_{3(1-y)}$, wherein y is from 0.01 to 0.99.

11. A semiconductor device according to claim 10, wherein the crystalline compound is a perovskite of formula wherein
y is from 0.01 to 0.70 or
y is from 0.20 to 0.60.

12. A semiconductor device according to claim 10, wherein the semiconductor device is an optoelectronic device, preferably wherein the semiconductor device is a photovoltaic device, a photodetector or a light-emitting device, more preferably wherein the semiconductor device is a photovoltaic device.

13. A semiconductor device according to claim 10, which semiconductor device comprises a layer of said semiconducting material, preferably wherein the layer of said semiconducting material has a thickness of from 5 nm to 10000 nm.

14. A semiconductor device according to claim 10, which semiconductor device comprises:
an n-type region comprising at least one n-type layer;
a p-type region comprising at least one p-type layer; and,
disposed between the n-type region and the p-type region:
a layer of said semiconducting material.

15. A semiconductor device according to claim 10, which semiconductor device is a tandem photovoltaic device and further comprises a layer of a second semiconductor material wherein the band gap of the second semiconductor material is lower than the band gap of the semiconductor material comprising the crystalline compound, preferably wherein the second semiconductor material comprises silicon, a perovskite, copper indium selenide (CIS), copper indium gallium diselenide (CIGS), CdTe, PbS or PbSe.

16. A semiconductor device which is a tandem photovoltaic device according to claim 15, wherein the tandem photovoltaic device comprises:
(i) a layer of silicon;
(ii) disposed on the layer of silicon, a layer of a transparent conducting oxide;
(iii) disposed on the layer of a transparent conducting oxide, an n-type region comprising at least one n-type layer;
(iv) disposed on the n-type region, a layer of said semiconducting material;

(v) disposed on the layer of said semiconducting material, a p-type region comprising at least one p-type layer; and (vi) disposed on the p-type region, a layer of an electrode material.

17. A semiconductor device according to claim 10, which device comprises
a layer of a transparent conducting oxide;
disposed on the layer of the transparent conducting oxide, a layer of an n-type metal oxide;
disposed on the layer of the n-type metal oxide, a layer of said crystalline compound; and
disposed on the layer of the crystalline compound, a layer of an electrode material.

18. A process for producing a layer of a crystalline compound, which crystalline compound comprises a perovskite of formula $Cs_{0.17}(H_2N-C(H)=NH_2)_{0.83}PbBr_{3y}I_{3(1-y)}$, wherein y is from 0.01 to 0.99,
which process comprises:
(a) disposing on a substrate a precursor composition comprising:
CsBr and/or CsI';
$(H_2N-C(H)=NH_2)Br$ and/or $(H_2N-C(H)=NH_2)I'$;
$PbBr_2$ and/or $PbI'_2$.

19. A process according to claim 18, wherein disposing on a substrate a precursor composition comprises:

(Ai) exposing the substrate to one or more vapours, which one or more vapours comprise said precursor composition; and
(Aii) allowing deposition of the one or more vapours onto the substrate to produce a layer of the crystalline compound thereon;
or
(Bi) disposing the precursor composition and one or more solvents on the substrate; and
(Bii) removing the one or more solvents to produce on the substrate a layer of crystalline compound.

20. A process according to claim 18, wherein the crystalline compound is a perovskite of formula wherein
y is from 0.01 to 0.70 or
y is from 0.20 to 0.60.

21. A process according to claim 18, wherein the precursor composition comprises:
CsI and/or CsBr;
$(H_2N-C(H)=NH_2)I$ and/or $(H_2N-C(H)=NH_2)Br$;
$PbI_2$;
$PbBr_2$; and
a polar aprotic solvent.

22. A process for producing a semiconductor device, which process comprises a process for producing a layer of a crystalline compound as defined in claim 18.

* * * * *

UNITED STATES PATENT AND TRADEMARK OFFICE
CERTIFICATE OF CORRECTION

PATENT NO. : 10,535,828 B2
APPLICATION NO. : 15/779174
DATED : January 14, 2020
INVENTOR(S) : Michael Saliba et al.

It is certified that error appears in the above-identified patent and that said Letters Patent is hereby corrected as shown below:

In the Specification

Column 2, Line 10, "(MAPb(I$_{(1-y)}$Br$_3$)$_3$)" should be --(MAPb(I$_{(1-y)}$Br$_y$)$_3$)--.

Column 2, Line 17, "(MAPb(I$_{(1-y)}$Br$_3$)$_3$)" should be --(MAPb(I$_{(1-y)}$Br$_y$)$_3$)--.

Column 3, Line 19, "Cs';" should be --Cs$^+$;--.

Column 3, Line 20, "(H$_2$N-C(H)=N H$_2$)';" should be --(H$_2$N-C(H)=NH$_2$)$^+$;--.

Column 3, Line 29, "Cs';" should be --Cs$^+$;--.

Column 3, Line 30, "(H$_2$N-C(H)=NH$_2$)';" should be --(H$_2$N-C(H)=NH$_2$)$^+$;--.

Column 3, Line 36, "Cs';" should be --Cs$^+$;--.

Column 3, Line 37, "(H$_2$N-C(H)=N H$_2$';" should be --(H$_2$N-C(H)=NH$_2$)$^+$;--.

Column 4, Line 37, "show s" should be --shows--.

Column 4, Line 41, "stead)-state" should be --steady-state--.

Column 6, Line 14, "Cs'," should be --Cs$^+$;--.

Column 6, Line 14, "(H$_2$N-C(H)=NH$_2$)';" should be --(H$_2$N-C(H)=NH$_2$)$^+$;--.

Column 6, Line 18, "Cs'," should be --Cs$^+$,--.

Column 6, Line 18, "(H$_2$N-C(H)=NH$_2$)'," should be --(H$_2$N-C(H)=NH$_2$)$^+$,--.

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,535,828 B2

Column 6, Line 53, "w ill" should be --will--.

Column 6, Line 61, "cu$^{2+}$" should be --Cu$^{2+}$--.

Column 7, Line 3, "Cs';" should be --Cs$^+$;--.

Column 11, Line 36, "ma)" should be --may--.

Column 12, Line 9 "III-VI" should be --II-VI--.

Column 15, Line 67, "Cs'," should be --Cs$^+$,--.

Column 15, Line 67, "NH$_3$CH$_3$'," should be --NH$_3$CH$_3$$^+$,--.

Column 16, Line 1, "=NH$_2$)')" should be --=NH$_2$)$^+$)--.

Column 18, Line 65, "0.0919 cm" should be --0.0919 cm$^{-2}$--.

Column 19, Line 28, "40 's" should be --40 fs--.

Column 21, Line 36, "~β mW" should be --~3 mW--.

Column 21, Line 45, "show n" should be --shown--.

Column 21, Line 60, "of E" should be --of E$_u$--.

Column 22, Line 38, "mobilities p for" should be --mobilities μ for--.

Column 23, Line 67, "if the) are" should be --if they are--.

In the Claims

Column 26, Claim 8, Line 15, "Cs$_{0.17}$N(H$_2$N-" should be --Cs$_{0.17}$(H$_2$N--.